(12) United States Patent
Kondoh

(10) Patent No.: US 9,080,858 B2
(45) Date of Patent: Jul. 14, 2015

(54) WAVEFRONT MEASURING APPARATUS, WAVEFRONT MEASURING METHOD, AND COMPUTER-READABLE MEDIUM STORING PROGRAM

(71) Applicant: CANON KABUSHIKI KAISHA, Tokyo (JP)

(72) Inventor: Takeshi Kondoh, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/481,627

(22) Filed: Sep. 9, 2014

(65) Prior Publication Data

US 2014/0376004 A1   Dec. 25, 2014

Related U.S. Application Data

(63) Continuation of application No. 13/561,824, filed on Jul. 30, 2012, now Pat. No. 8,859,977.

(30) Foreign Application Priority Data

Aug. 3, 2011 (JP) ................................. 2011-170288
Jun. 19, 2012 (JP) ................................. 2012-137921

(51) Int. Cl.
*G01N 23/083* (2006.01)
*G01B 11/14* (2006.01)
*G01N 23/04* (2006.01)
*G21K 1/02* (2006.01)

(52) U.S. Cl.
CPC .............. *G01B 11/14* (2013.01); *G01N 23/046* (2013.01); *G01N 23/083* (2013.01); *G21K 1/02* (2013.01); *G21K 2207/005* (2013.01)

(58) Field of Classification Search
CPC ..... G01B 11/14; G01N 23/04; G01N 23/046; G01N 23/08; G01N 23/083; G01T 1/24; G01T 1/29; G21K 1/02; G21K 2207/005
See application file for complete search history.

(56) References Cited

U.S. PATENT DOCUMENTS

2005/0286680 A1* 12/2005 Momose ......................... 378/62
2010/0290590 A1* 11/2010 Ouchi et al. .................... 378/62

* cited by examiner

*Primary Examiner* — Mark R Gaworecki
(74) *Attorney, Agent, or Firm* — Canon USA Inc. IP Division

(57) ABSTRACT

A wavefront measuring apparatus includes an optical element forming a periodic pattern by light, a detector having pixels to detect the light, and a computer computing, based on detection results of the detector, wavefront information at positions in a wavefront of the light transmitted through or reflected by a specimen. The detector detects a first periodic pattern formed by the light, and a second periodic pattern formed by the light and shifted in phase from the first periodic pattern. The computer computes the wavefront information at one of the positions by using a result detected in a first pixel of the pixels when detecting the first periodic pattern, a result detected in a second pixel of the pixels when detecting the first periodic pattern, the second pixel being positioned within three pixels from the first pixel, and a result detected in the first pixel when detecting the second periodic pattern.

16 Claims, 25 Drawing Sheets

140a

8 μm 141a 142a

140b

8 μm 141b 142b

- - - - EXAMPLE 6 (INTERMEDIATE METHOD)
·········· COMPARATIVE EXAMPLE 5 (PHASE SHIFT)
—·— COMPARATIVE EXAMPLE 6 (FOURIER)
——— TRUE VALUE (PHANTOM)

WAVEFRONT MEASURING APPARATUS, WAVEFRONT MEASURING METHOD, AND COMPUTER-READABLE MEDIUM STORING PROGRAM

CROSS-REFERENCE TO RELATED APPLICATIONS

This application is a Continuation of co-pending U.S. patent application Ser. No. 13/561,824, filed Jul. 30, 2012, which claims foreign priority benefit of Japanese Patent Application No. 2011-170288 filed Aug. 3, 2011 and Japanese Patent Application No. 2012-137921 filed Jun. 19, 2012, all of which are hereby incorporated by reference herein in their entirety.

BACKGROUND OF THE INVENTION

1. Field of the Invention

Disclosed aspects of the embodiments relate to a wavefront measuring apparatus, a wavefront measuring method, and a computer-readable medium storing a program for use in them. More particularly, the disclosed aspects relate to a wavefront measuring apparatus, a wavefront measuring method, and a program, which are adapted for deriving wavefront information from a periodic pattern (periodic pattern of light) that has been modulated by a specimen (i.e., an object to be analyzed).

2. Description of the Related Art

In the optical metrology, information of a specimen is often derived by analyzing modulation of a periodic pattern. As analytical techniques for the periodic pattern, there are known a phase shifting method and a windowed Fourier transform method. The phase shifting method and the windowed Fourier transform method are described in brief by taking, as an example, a periodic pattern I(x, y) expressed by the following formula (1). For simplicity, a one-dimensional periodic pattern is discussed below, but the following discussion is similarly applied to a two-dimensional periodic pattern as well:

$$I(x,y)=a(x,y)+b(x,y)\cos[\omega_x x+\phi(x,y)] \quad (1)$$

where a(x, y) is a background irradiance, b(x, y) is an amplitude distribution of the periodic pattern, $\omega_x$ is a spatial carrier frequency, and $\phi(x, y)$ is a phase distribution or a differential phase distribution induced by the specimen.

The phase shifting method is a technique of measuring the wavefront of light having transmitted through a specimen by using a plurality of periodic patterns that have phases shifted from one another, and obtaining information of the specimen. The phase shifting method is featured in that the information of the specimen is independently obtained from the intensity of the light detected for each of pixels. Let consider, as an example, the case of extracting the information of the specimen from three periodic patterns having phases shifted from one another, which are expressed by the following formulae (2):

$$I_1(x, y) = a(x, y) + b(x, y)\cos[\omega_x x + \varphi(x, y)] \quad (2)$$

$$I_2(x, y) = a(x, y) + b(x, y)\cos\left[\omega_x x + \varphi(x, y) + 2\pi\frac{1}{3}\right]$$

$$I_3(x, y) = a(x, y) + b(x, y)\cos\left[\omega_x x + \varphi(x, y) + 2\pi\frac{2}{3}\right]$$

According to The Japan Society of Applied Physics, Atsushi Momose, Wataru Yashiro, Yoshihiro Takeda, Yoshio Suzuki and Tadashi Hattori, "Phase Tomography by X-ray Talbot Interferometry for Biological Imaging", Japanese Journal of Applied Physics, Vol. 45, No. 6A, pp. 5254-5256 (2006), Japan, the phase distribution or the differential phase distribution induced by a specimen is obtained from the following formula (3). In the formula (3), arg[•] denotes a phase component of the expression within [ ].

$$\varphi(x, y) = \arg\left[\sum_{k=1}^{3} I_k(x, y)\exp\left[-2\pi i\frac{k-1}{3}\right]\right] \quad (3)$$

Because the obtained phase distribution or differential phase distribution is given as a value wrapped between $-\pi$ and $\pi$, it is to be unwrapped.

Thus, when the periodic pattern capable of being expressed by the formula (1) is used, the wavefront information of the light having transmitted through the specimen is derived by the phase shifting method if there are three or more periodic patterns, and the phase distribution or the differential phase distribution of the specimen is obtained.

On the other hand, the windowed Fourier transform method is featured in that the wavefront information of the light having transmitted through the specimen may be derived from even one periodic pattern. Details of the windowed Fourier transform method is discussed in Elsevier, Qian Kemao, "Two-dimensional windowed Fourier transform for fringe pattern analysis: Principles, applications and implementations", Volume 45, Issue 2, pages 304-317, Optics and Lasers in Engineering, 2007, The Netherlands. The windowed Fourier transform method is described in brief below. The formula (1) is rewritten into the following formulae (4).

$$I(x, y) = a(x, y) + c(x, y)\exp(i\omega_x x) + c^*(x, y)\exp[-i\omega_x x] \quad (4)$$

$$c(x, y) = \frac{b(x, y)}{2}\exp[i\varphi(x, y)],$$

$$c^*(x, y) = \frac{b(x, y)}{2}\exp[-i\varphi(x, y)]$$

According to the windowed Fourier transform method, the wavefront information of the light having transmitted through the specimen is derived by locally cutting out the periodic pattern with a window function, and determining Fourier coefficients of a zeroth-order spectrum and a spatial carrier frequency. In other words, a(x, y), c(x, y) and c*(x, y) are obtained by the following formulae (5):

$$a(x,y)=\iint I(\eta,\nu)g(\mu-x,\nu-y)d\mu d\nu$$

$$c(x,y)=\iint I(\eta,\nu)g(\mu-x,\nu-y)\exp[-i\omega_x\mu]d\mu d\nu$$

$$c^*(x,y)=\iint I(\eta,\nu)g(\mu-x,\nu-y)\exp[i\omega_x\mu]d\mu d\nu \quad (5)$$

where the window function is g(x, y), and $\mu$ and $\nu$ are each a variable of integration. Further, as in the phase shifting method, because the obtained wavefront information is given as a value wrapped between $-\pi$ and $\pi$, it is to be unwrapped.

In the phase shifting method, when the periodic pattern is expressed by the formula (1), at least three periodic patterns having phases shifted from one another are employed for the reason that there are three unknowns. More periodic patterns are to be employed in order to obtain phase distributions or differential phase distributions in two directions from two-dimensional periodic patterns.

Meanwhile, with the windowed Fourier transform method, the information of the specimen is obtained from one periodic pattern. However, the wavefront information of the light is not independently derived from the detection result for each pixel, but by using the detection results of surrounding pixels as well. Accordingly, accuracy of the wavefront information obtained with the windowed Fourier transform method is lower than that obtained with the phase shifting method.

SUMMARY OF THE INVENTION

In view of the problems described above, the present disclosure provides a wavefront measuring method, a wavefront measuring apparatus, and a computer-readable medium storing a program, which may accurately derive wavefront information by using the windowed Fourier transform method even from fewer periodic patterns than used in the phase shifting method.

According to an embodiment, there is provided a wavefront measuring apparatus including an optical element arranged to form a periodic pattern by light emitted from a light source, a detector having a plurality of pixels to detect the light that enters the detector from the optical element, and a computer configured to compute, based on detection results of the detector, wavefront information at a plurality of positions in a wavefront of the light having transmitted through or having been reflected by a specimen, wherein the detector detects a first periodic pattern formed by the light from the optical element, and a second periodic pattern formed by the light from the optical element and having a phase shifted with respect to a phase of the first periodic pattern, and wherein the computer computes the wavefront information at one of the plural positions by using a detection result detected in a first pixel of the plural pixels at time of detecting the first periodic pattern, a detection result detected in a second pixel of the plural pixels at the time of detecting the first periodic pattern, the second pixel being positioned within three pixels from the first pixel, and a detection result detected in the first pixel at time of detecting the second periodic pattern.

Further features of the present invention will become apparent from the following description of exemplary embodiments with reference to the attached drawings.

DESCRIPTION OF THE EMBODIMENTS

Figure 1:
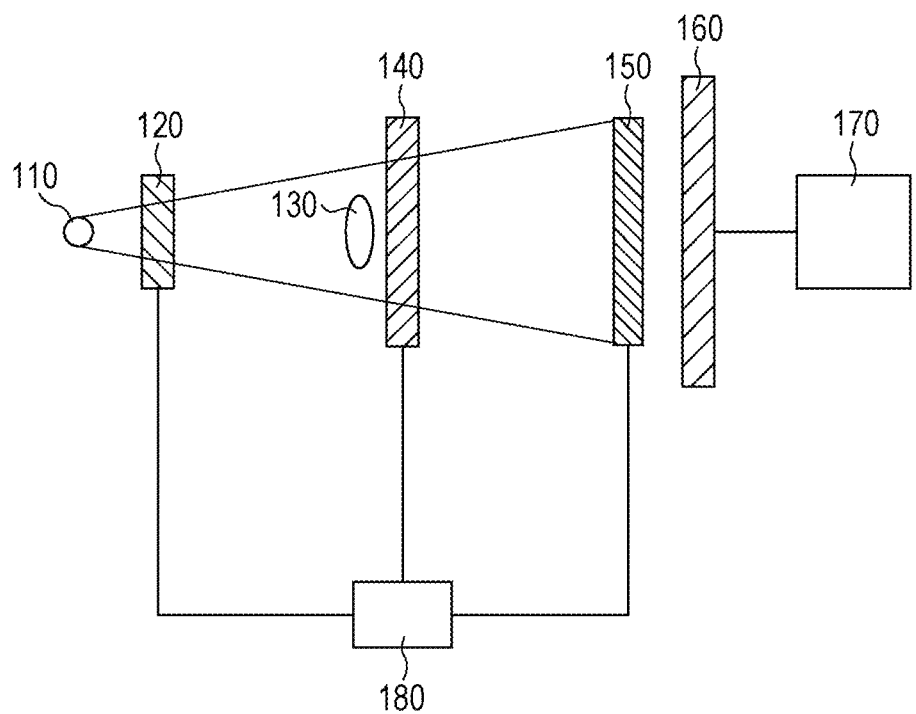
FIG. 1 is an overall view of a wavefront measuring apparatus according to a first embodiment.

First and second embodiments will be described below with reference to the accompanying drawings. It is to be noted that, in the drawings, the same components are denoted by the same reference numerals and duplicate descriptions are omitted. The first and second embodiments are in common in that a periodic pattern of light (i.e., a periodic pattern) is detected plural times, a virtual periodic pattern is obtained from the plural periodic patterns, and information regarding the wavefront of the light is derived by using the virtual periodic pattern.

First Embodiment

The first embodiment is described in connection with a wavefront measuring apparatus in which the wavefront of light having transmitted through a specimen is measured in accordance with the phase shifting method.

The wavefront measuring apparatus according to this embodiment is an X-ray imaging apparatus (hereinafter referred to also as an "X-ray phase imaging apparatus"), which performs X-ray phase imaging by employing the Talbot-Lau interference method. However, embodiments are limited to neither the Talbot-Lau interference method nor the wavefront measuring apparatus that performs the X-ray phase imaging. The embodiments may also be applied to general techniques for measuring modulation of a periodic pattern, the modulation being caused by a specimen.

Because the X-ray phase imaging apparatus employing the Talbot-Lau interference method is discussed in detail in SPIE, Timm Weitkamp, Christian David, Christian Kottler, Oliver Bunk, and Franz Pfeiffer, "Tomography with grating interferometers at low-brilliance sources", Proceedings of SPIE Vol. 6318, 63180S-1 (2006), USA an outline is described here.

FIG. 1 is a schematic view of the wavefront measuring apparatus (X-ray phase imaging apparatus) according to the first embodiment, the apparatus employing the Talbot-Lau interference method.

The wavefront measuring apparatus 1 according to the first embodiment includes an X-ray source 110 as a light source, a source grating 120 for dividing X-ray radiation from the X-ray source 110 into a plurality of beams, a phase-type diffraction grating (hereinafter referred to as a "phase grating") 140, and a shield grating 150. The phase grating 140 and the shield grating 150 are optical elements for forming a periodic pattern with the X-ray beams from the source grating 120. The wavefront measuring apparatus 1 further includes a detector 160 for detecting an X-ray pattern from the shield grating 150, and a computer 170 serving as an arithmetic unit (processing unit) that executes calculations on the basis of detection results of the detector 160. In addition, the wavefront measuring apparatus 1 includes an actuator 180 as a moving unit that moves at least one of the source grating 120, the diffraction (phase) grating 140, the shield grating 150, and the detector 160.

The operation of the wavefront measuring apparatus including those components is described below.

The X-ray radiation from the light source (X-ray source) 110 is delivered to the source grating 120.

The source grating 120 has an X-ray transmitting portion and an X-ray shielding portion, and it divides the X-ray radiation from the X-ray source 110 into plural X-ray beams.

The X-ray beam divided by the source grating 120 is delivered to impinge upon a specimen 130, and the X-ray having transmitted through the specimen 130 is diffracted by the diffraction (phase) grating 140.

The phase grating 140 is a phase-type diffraction grating for periodically changing the phase of the X-ray. The phase grating 140 has a phase reference portion and a phase shift portion, which are periodically arrayed. When the phase grating 140 diffracts the X-ray having transmitted through the specimen 130, an interference pattern of the light (X-ray) is formed at a predetermined distance that is called the Talbot distance. That interference pattern is a periodic pattern (X-ray periodic pattern). The term "periodic pattern" in the present specification includes a pattern that does not have a fixed (predetermined) period even when the specimen is not arranged between the light source and the periodic pattern. For example, a pattern in which the period is gradually changed as a distance from a pattern center increases is also called the periodic pattern. Accordingly, as used herein the term "period pattern" may include patterns of a fixed (predetermined) period or patterns of a variable period.

The shield grating 150 is arranged at a position spaced from the phase grating 140 by the Talbot distance such that the interference pattern is formed on the shield grating 150. The shield grating 150 has a light (X-ray) shielding portion (hereinafter referred to as a "shielding portion") and a light (X-ray) transmitting portion (hereinafter referred to as a "transmitting portion"), which are periodically arrayed. A period at which the shielding portion and the transmitting portion are arrayed slightly differs from a period of the interference pattern formed on the shield grating 150. Therefore, the X-ray having transmitted through the shield grating 150 forms a moiré that is an X-ray periodic pattern. In this embodiment, the moiré formed through the phase grating 140 and the shield grating 150 is detected, and information of the specimen is obtained from the moiré. It should be understood that in general a moiré is created, for example, when two gratings have slightly different mesh sizes (grating periods), as described above, but the moiré may also be created when two gratings are spatially overlaid at an angle.

The detector 160 has a plurality of pixels for detecting the intensity of light (X-ray) and detects the moiré formed by the light having transmitted through the shield grating 150.

Based on detection results of the detector 160, the computer 170 computes wavefront information at plural positions of a wavefront of the light forming the moiré. The wavefront information computed here represents at least one of phase, amplitude, and scattering parameters included in the wavefront. Because the light forming the moiré is modulated by the specimen 130, the wavefront information computed by the computer 170 contains information of the specimen 130.

An analytical method executed by the computer 170 to obtain the wavefront information will be described later.

The actuator 180 moves or rotates the interference pattern and the shield grating 150 relatively by displacing at least one of the source grating 120, the phase grating 140, and the shield grating 150. The actuator 180 may perform both the movement (translation) and the rotation. As a result, the phase of the moiré is shifted. The displacement may be a movement changing a position or a rotational movement changing a tilt. While the interference pattern and the shield grating are relatively moved and/or rotated in this embodiment, a moving unit is just to be capable of shifting the phase of the moiré (interference pattern). For example, the phase of the moiré may be shifted by moving the detector 160.

The analytical method of computing the wavefront information with the computer 170 in this embodiment will be described below.

As mentioned above, the analytical method based on the phase shifting method is described in this embodiment.

The computer 170 in this embodiment computes the wavefront information by using a first periodic pattern (first X-ray periodic pattern) detected by the detector 160, and a second periodic pattern (second X-ray periodic pattern) having a phase different from that of the first periodic pattern, thereby obtaining the information of the specimen. The first periodic pattern and the second periodic pattern are each the moiré formed by the light having transmitted through the shield grating 150. In this embodiment, the second periodic pattern is detected by, after detecting the first periodic pattern, moving the interference pattern and the shield grating relatively by the actuator 180 to shift the phase of the moiré, and detecting the moiré again by the detector 160. However, if the relative movement distance between the interference pattern and the shield grating is equal to an integer multiple of the period of the interference pattern or the shield grating, the phase of the formed moiré is not shifted (namely, a shift amount is an integer multiple of $2\pi$). Therefore, the second periodic pattern is not detected (namely, the first periodic pattern is detected again). For that reason, when the phase of the moiré is shifted by relatively moving the interference pattern and the shield grating to change a positional relationship therebetween, the relative movement is performed such that the relative movement distance between the interference pattern and the shield grating is not equal to an integer multiple of the period of the interference pattern or the shield grating.

Here, the moiré intensity of the first periodic pattern is denoted by $I_1$ and the moiré intensity of the second periodic pattern is denoted by $I_2$.

In this embodiment, the information of the specimen is obtained from $I_1$ and $I_2$ expressed by the following formulae (6):

$$I_1(x,y)=a(x,y)+b(x,y)\cos[\omega_x x+\phi(x,y)]$$

$$I_2(x,y)=a(x,y)+b(x,y)\cos[\omega_x(x+\alpha)+\phi(x,y)] \quad (6)$$

where $a(x, y)$ is a background periodic pattern, $b(x, y)$ is an amplitude distribution of the moiré, $\omega_x$ is a spatial carrier frequency, $\omega_x\alpha$ is a phase shift amount (phase difference) between $I_4$ and $I_2$, and $\phi(x, y)$ is a differential phase distribution of the specimen. Further, a unit of each of x and y is a pixel.

Virtual moirés $I_3$ and $I_4$ expressed by the following formulae (7) are obtained from $I_1$ and $I_2$:

$$I_3(x,y)=I_1(x-m,y)$$

$$I_4(x,y)=I_2(x-n,y) \qquad (7)$$

In the formulae (7), m and n are each an integer other than 0, and they may be the same number or different numbers. When changes of a(x, y), b(x, y) and $\phi(x, y)$ are sufficiently moderate with respect to $\omega_x$, the formulae (7) may be rewritten into the following formulae (8):

$$I_3(x, y) = a(x-m, y) + b(x-m, y)\cos[\omega_x(x-m) + \varphi(x, y)] \qquad (8)$$
$$\approx a(x, y) + b(x, y)\cos[\omega_x(x-m) + \varphi(x, y)]$$

$$I_4(x, y) = a(x-m, y) + b(x-m, y)\cos[\omega_x(x-m+\alpha) + \varphi(x-m, y)]$$
$$\approx a(x, y) + b(x, y)\cos[\omega_x(x-m+\alpha) + \varphi(x, y)]$$

The formulae (6), (7) and (8) are rewritten into the following formulae (9):

$$I_1(x, y) = a(x, y) + \qquad (9)$$
$$\frac{b(x, y)}{2}(\exp[i\omega_x x]\exp[i\varphi(x, y)] + \exp[-i\omega_x x]\exp[-i\varphi(x, y)])$$

$$I_2(x, y) = a(x, y) + \frac{b(x, y)}{2}(\exp[i(\omega_x(x+\alpha))]\exp[i\varphi(x, y)] +$$
$$\exp[-i(\omega_x(x+\alpha))]\exp[-i\varphi(x, y)])$$

$$I_3(x, y) \approx a(x, y) + \frac{b(x, y)}{2}(\exp[i(\omega_x(x-m))]\exp[i\varphi(x, y)] +$$
$$\exp[-i(\omega_x(x-m))]\exp[-i\varphi(x, y)])$$

$$I_4(x, y) \approx a(x, y) + \frac{b(x, y)}{2}(\exp[i(\omega_x(x-m+\alpha))]\exp[i\varphi(x, y)] +$$
$$\exp[-i(\omega_x(x-m+\alpha))]\exp[-i\varphi(x, y)])$$

Further, the formulae (9) is expressed by the following formula (10) in the form of a matrix:

$$\begin{pmatrix} I_1(x, y) \\ I_2(x, y) \\ I_3(x, y) \\ I_4(x, y) \end{pmatrix} \approx \qquad (10)$$

$$\begin{pmatrix} 1 & \exp[i\omega_x x] & \exp[-i\omega_x x] \\ 1 & \exp[i(\omega_x(x+\alpha))] & \exp[-i(\omega_x(x+\alpha))] \\ 1 & \exp[i\omega_x(x-m)] & \exp[-i\omega_x(x-m)] \\ 1 & \exp[i(\omega_x(x-m+\alpha))] & \exp[-i(\omega_x(x-m+\alpha))] \end{pmatrix} \begin{pmatrix} a(x, y) \\ c(x, y) \\ c*(x, y) \end{pmatrix}$$

$$c(x, y) = \frac{b(x, y)}{2}\exp[i\varphi(x, y)],$$

$$c^*(x, y) = \frac{b(x, y)}{2}\exp[-i\varphi(x, y)]$$

Accordingly, given that a pseudo inverse matrix of a matrix A is $A^{-1}$, a(x, y), c(x, y) and c*(x, y) are obtained from the following formula (11), while b(x, y) and $\phi(x, y)$ are obtained from c(x, y) and c*(x, y):

$$\begin{pmatrix} a(x, y) \\ c(x, y) \\ c^*(x, y) \end{pmatrix} \approx \qquad (11)$$

$$\begin{pmatrix} 1 & \exp[i\omega_x x] & \exp[-i\omega_x x] \\ 1 & \exp[i(\omega_x(x+\alpha))] & \exp[-i(\omega_x(x+\alpha))] \\ 1 & \exp[i\omega_x(x-m)] & \exp[-i\omega_x(x-m)] \\ 1 & \exp[i(\omega_x(x-m+\alpha))] & \exp[-i(\omega_x(x-m+\alpha))] \end{pmatrix}^{-1} \begin{pmatrix} I_1(x, y) \\ I_2(x, y) \\ I_3(x, y) \\ I_4(x, y) \end{pmatrix}$$

Thus, the wavefront information at one position (x, y) is obtained from the first periodic pattern ($I_1$) and the second periodic pattern ($I_2$).

Because the Talbot-Lau interferometer is a shearing interferometer, differentiated data of the wavefront information (i.e., differential wavefront information) is obtained. Therefore, a differential phase image of the specimen is obtained by mapping the $\phi(x, y)$. Moreover, a phase image is obtained from the differential phase image, and an absorption image and a scattering image of the specimen are obtained respectively from a(x, y) and b(x, y). While $\phi(x, y)$ obtained in this embodiment represents a differential phase distribution of the specimen because the Talbot-Lau interferometer is a shearing interferometer, $\phi(x, y)$ represents a phase distribution of the specimen when an interferometer other than the shearing interferometer, such as a Michelson interferometer or a Fizeau interferometer, is used. Therefore, a phase image is obtained by mapping $\phi(x, y)$ that has been obtained with the interferometer other than shearing interferometer.

Figure 2A:
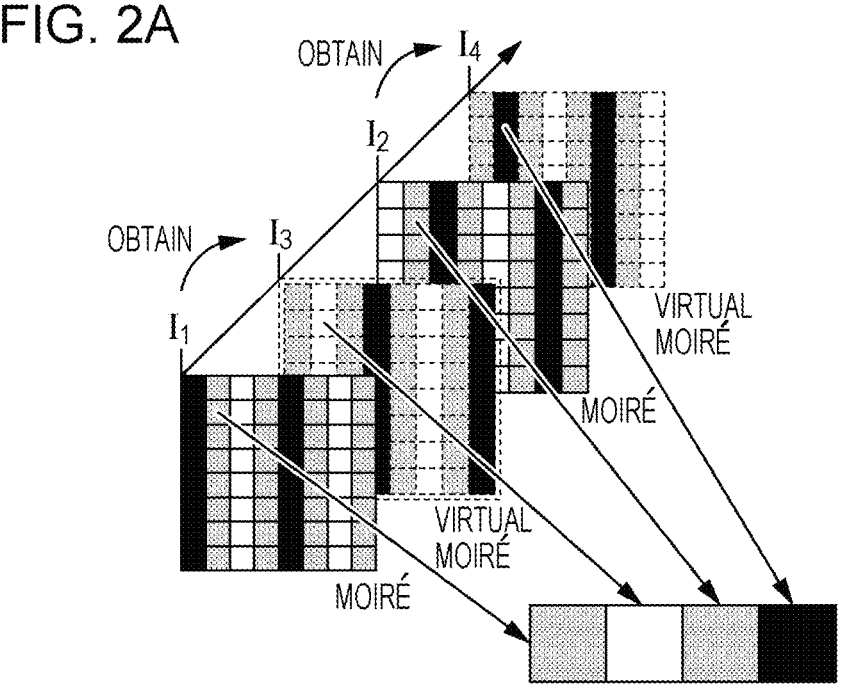
FIGS. 2A and 2B are each a conceptual view of a wavefront measuring method according to the first embodiment.
Figure 2B:
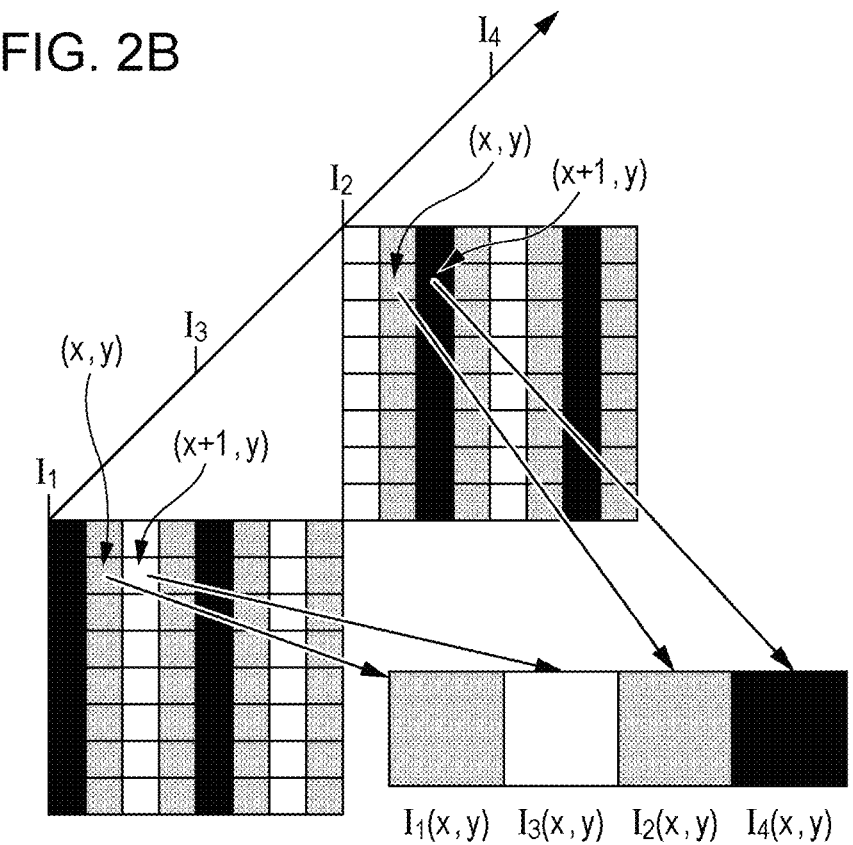

FIGS. 2A and 2B are each a conceptual view illustrating the analytical method executed by the computer 170 in this embodiment. FIG. 2A illustrates the concept of deriving the information of the specimen by, as described above, obtaining $I_3$ from $I_1$ and $I_4$ from $I_2$, respectively, and by carrying out the phase shifting method based on the actually detected moiré ($I_1$, $I_2$) and the virtual moiré ($I_3$, $I_4$).

$I_3$ is obtained from $I_4$ by a method using the formula (7), and the intensity of X-ray (light) at particular coordinates (x, y) within $I_3$ is provided as the intensity of X-ray at particular coordinates (x−m, y) within $I_1$, which differ from the particular coordinates (x, y). $I_4$ is similarly obtained from $I_2$.

FIG. 2B illustrates an analytical method executed by the computer 170 in accordance with the above-described concept.

Thus, FIG. 2B is a conceptual view illustrating the analytical method executed by the computer 170 in this embodiment on condition that m and n are each +1. As illustrated in FIG. 2B, the information of the specimen at (x, y) is obtained by carrying out the phase shifting method based on the detection results of the X-ray intensity at (x, y) in $I_1$, (x, y) in $I_2$, (x+1, y) in $I_1$, which is given as (x, y) in $I_3$, and (x+1, y) in $I_2$, which is given as (x, y) in $I_4$.

To explain the analytical method used in this embodiment in another way, a pixel where the X-ray intensity at (x, y) is detected is defined as a first pixel, and a pixel where the X-ray intensity at (x−m, y) is detected is defined as a second pixel. Further, m and n are defined as the same value. In this embodiment, the wavefront information is derived by restoring phases on condition that a detection result ($I_1$(x, y)) of the first pixel at the time of detecting the first periodic pattern ($I_1$), a detection result ($I_1$(x+m, y)) of the second pixel at the time of detecting $I_1$, a detection result ($I_2$(x, y)) of the first pixel at the time of detecting the second periodic pattern ($I_2$), and a detection result ($I_2$(x+n, y)) of the second pixel at the time of detecting $I_2$ are regarded respectively as detection results of the first pixel ((x, y)) at the times of detecting $I_1$, $I_3$, $I_2$ and $I_4$. Here, the expression "restoring phases on condition that those detection results are regarded respectively as detection results of the first pixel ((x, y)) at the times of detecting $I_1$, $I_3$, $I_2$ and $I_4$" implies that phases are restored by using a calculation method used in the phase shifting method by regarding the above-mentioned four detection results respectively as detection results of the first pixel ((x, y)) at the times of detecting $I_1$, $I_3$, $I_2$ and $I_4$. The calculation method used in the phase shifting method may be executed by using the above-mentioned formula (11) or another calculation formula. In such a manner, the wavefront information of the X-ray (light) having entered the first pixel is derived. Furthermore, the phase shifting method may be carried out by regarding $I_1(x, y)$, $I_1(x+m, y)$, $I_2(x, y)$, and $I_2(x+n, y)$ respectively as detection results of the second pixel at the times of detecting $I_1$, $I_3$, $I_2$ and $I_4$. In that case, the wavefront information of the X-ray (light) having entered the second pixel is derived. However, the derived wavefront information is the same regardless of whether $I_1(x, y)$, $I_1(x+m, y)$, $I_2(x, y)$, and $I_2(x+n, y)$ are regarded as detection results of the first pixel or the second pixel.

Alternatively, m and n may take different values from each other. For example, a similar analysis to that in this embodiment may be executed by using the detection result of the first pixel at the time of detecting $I_1$, the detection result of the second pixel at the time of detecting $I_1$, the detection result of the first pixel at the time of detecting $I_2$, and the detection result of a pixel, which is neither the first pixel nor the second pixel, at the time of detecting $I_2$. In that case, the phase shifting method may be carried out by regarding the above-mentioned detection results respectively as the detection results of the first pixel at the times of detecting $I_1$, $I_3$, $I_2$ and $I_4$.

Moreover, even when the phase difference ($\omega_x \alpha$) between $I_1$ and $I_2$ is equal to a phase difference between the light detected in the first pixel and the light detected in the second pixel, the phase shifting method may be carried out by using $I_1(x, y)$, $I_1(x+m, y)$, $I_2(x, y)$, and $I_2(x+n, y)$.

In that case, $I_1(x+m, y)$ and $I_2(x, y)$ are the same (precisely speaking, they slightly differ from each other because the X-rays having transmitted through different portions of the specimen are detected). In view of that point, the phase shifting method may be carried out by regarding one of three (i.e., $I_1(x+m, y)$, $I_2(x, y)$, and a mean of $I_1(x+m, y)$ and $I_2(x, y)$) as $I_2(x, y)$, $I_1(x, y)$ as $I_1(x, y)$, and $I_2(x+n, y)$ as $I_3(x, y)$, respectively. When a formula representing the moiré has three unknowns as in the formula (1), the computer 170 in this embodiment may execute the analytical method if there are three or more moirés including a virtual moiré. Furthermore, if there are three or more moirés including a virtual moiré, the phase shifting method may be carried out on condition that m and n are each an integer other than 0, as described above, without being limited to ±1. However, a smaller absolute value of each of m and n is more beneficial because changes of a(x, y), b(x, y) and φ(x, y) become more moderate. A beneficial range of the absolute value of each of m and n is 1 to 3, and a more beneficial range is just 1. Even more beneficially, m=n is satisfied.

When the absolute value of each of m and n is 3, the second pixel is located at a three-pixel position counting from the first pixel. When the absolute value of each of m and n is 1, the second pixel is located adjacent to the first pixel. In other words, when the first pixel and the second pixel are adjacent to each other, the second pixel is located at a one-pixel position counting from the first pixel.

Phase shift amounts of periodic patterns used in a general phase shifting method are beneficially the same. For example, when an analysis is executed by using four moirés, phases of the four moirés are beneficially shifted by the same amount, i.e., (½)π. Similarly, it is beneficial in this embodiment that the phase shifting amounts of $I_1$, $I_2$, $I_3$ and $I_4$ are the same. Thus, given that m=n=±1 is held and a period of the moiré (periodic pattern) in units of pixel size is P (P=4 when the period of the moiré is 80 μm and the pixel size is 20 μm), the analysis is executed by using $I_2$ and $I_2$, which satisfy α=P/2.

In short, according to this embodiment, the information of the specimen is obtained by computing the first virtual periodic pattern ($I_3$) and the second virtual periodic pattern ($I_4$) from the first periodic pattern ($I_4$) and the second periodic pattern ($I_2$), respectively, and by applying the phase shifting method to those four periodic patterns.

The analytical method for the first periodic pattern and the second periodic pattern by the computer 170 has been described above. The above-described calculations may be executed on the computer 170 by installing, in the computer 170, a program that instructs the computer 170 to execute the above-described calculations.

While, in this embodiment, a moiré is formed by using the shield grating and the moiré is detected and analyzed, an interference pattern, not a moiré, may be directly detected and analyzed in which case shield grating is not needed.

By using the shield grating as in this embodiment, a detector having a resolution distance larger than the pitch of the interference pattern may be used.

Second Embodiment

A method of deriving the wavefront information by using a wavefront measuring method based on the windowed Fourier transform method is described in a second embodiment.

The configuration of the second embodiment is the same as that of the first embodiment except for a calculation method executed by a computer.

As in the first embodiment, a computer in the second embodiment derives the wavefront information by computing virtual periodic patterns from both the first periodic pattern detected by the detector 160 and the second periodic pattern having a phase difference with respect to the first periodic pattern, and by analyzing the virtual periodic patterns. However, the second embodiment differs from the first embodiment in a method of computing the virtual periodic patterns and in an analytical method of computing the wavefront information from the virtual periodic patterns. Furthermore, as in the first embodiment, the first periodic pattern and the second periodic pattern are each a periodic pattern of a moiré that is formed by light having transmitted through the shield grating 150. In the second embodiment, the moiré of the first periodic pattern is denoted by $I_5$, and the moiré of the second periodic pattern is denoted by $I_6$.

In this embodiment, the wavefront information is derived from $I_5$ and $I_6$ expressed by the following formulae (12):

$$I_5(x,y)=a(x,y)+b(x,y)\cos[\omega_x x+\phi(x,y)]$$

$$I_6(x,y)=a(x,y)+b(x,y)\cos[\omega_x(x+\alpha)+\phi(x,y)] \quad (12)$$

where $\omega_x \alpha$ is a phase difference between $I_5$ and $I_6$, and α is an integer other than 0.

A virtual moiré I(x, y) is computed by combining the moirés $I_5(x, y)$ and $I_6(x, y)$ with each other. The virtual moiré computed by combining the moirés is also referred to as a "composite moiré (composite periodic moiré)" hereinafter. When the information of the specimen at a pixel ($x_0$, $y_0$) is to be obtained, I(x, y) is expressed, for example, by the following formula (13):

$$I(x, y) = \begin{cases} I_5(x, y), & \text{for } x \le x_0 + \left[\frac{P-\alpha}{2}\right] \\ I_6(x-\alpha, y), & \text{for } x \ge x_0 + \left[\frac{P-\alpha}{2}\right] + 1 \end{cases} \quad (13)$$

where [A] is a floor function and it indicates a maximum integer equal to or less than A (e.g., [2.5]=2, and [2]=2).

Further, P represents a moiré period in units of pixel size. When P−α is an even number, the following formula (14) may be used:

$$I(x, y) = \begin{cases} I_5(x, y), & \text{for } x \le x_0 + \left[\frac{P-\alpha}{2}\right] - 1 \\ I_6(x-\alpha, y), & \text{for } x \ge x_0 + \left[\frac{P-\alpha}{2}\right] \end{cases} \quad (14)$$

A differential phase image is obtained from the computed I(x, y) in accordance with the formulae (5).

While various window functions may be optionally used as the window function, a Gauss function is used in this embodiment. In this embodiment, the information of the specimen is derived from the Fourier coefficients after locally cutting out the moiré with the window function. However, the information of the specimen may be obtained by taking the Fourier transform of the moiré, cutting out peaks of a Fourier spectrum, and taking the inverse Fourier transform to cancel a tilt attributable to the moiré. Such a process is expressed by the following formula (15):

$$a(x,y) = \mathcal{F}^{-1}[IS(\xi,\eta) \times G(\xi,\eta)]$$

$$c(x,y) = \exp[-i\omega_x x] \times \mathcal{F}^{-1}[IS(\xi,\eta) \times G(\xi-\omega_x,\eta)]$$

$$c^*(x,y) = \exp[i\omega_x x] \times \mathcal{F}^{-1}[IS(\xi,\eta) \times G(\xi+\omega_x,\eta)] \quad (15)$$

where $G(\zeta, \eta)$ is a window function, $IS(\zeta, \eta)$ is a Fourier spectrum of the moiré I(x, y), $\zeta$ and $\eta$ are each a spatial frequency. $F^{-1}$ represents the inverse Fourier transform.

Figure 3:
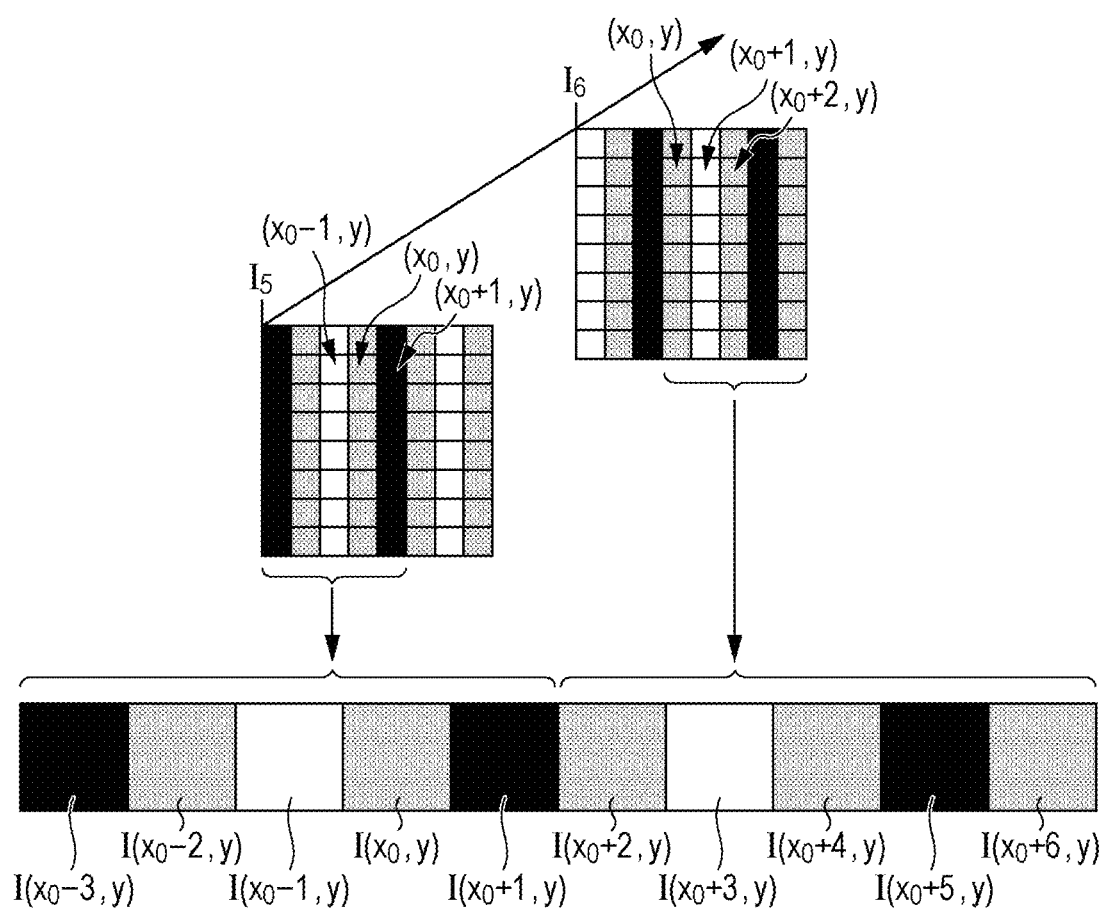
FIG. 3 is a conceptual view of a wavefront measuring method according to a second embodiment.

FIG. 3 is a conceptual view illustrating the analytical method executed by the computer in this embodiment. FIG. 3 illustrates the concept of computing I(x, y) by using $I_5(x, y)$ and $I_6(x, y)$, as described above. While α=2 and P=4 are held and P−α is an even number, the formula (13) is used in FIG. 3.

To explain the analytical method used in this embodiment in another way, a pixel where the X-ray intensity at $(x_0, y)$ is detected is defined as a first pixel, and a pixel where the X-ray intensity at $(x_0-1, y)$ is detected is defined as a second pixel. In this embodiment, a detection result $(I_5(x_0, y))$ of the first pixel at the time of detecting $I_5$ is given as a detection result $(I(x_0, y))$ of the first pixel at the time of detecting I, and a detection result $(I_5(x_0-1, y))$ of the second pixel at the time of detecting $I_5$ is given as a detection result $(I(x_0-1, y))$ of the second pixel at the time of detecting I. Further, a detection result $(I_6(x_0, y))$ of the first pixel at the time of detecting $I_6$ is given as a detection result $(I(x_0+P-\alpha, y))$ of a pixel, which is neither the first pixel nor the second pixel, at the time of detecting I. In such a manner, the composite moiré I is computed by using $I_5$ and $I_6$. Moreover, the wavefront information of the X-ray at one position $(x_0, y)$ is computed by using the composite moiré I and the Fourier transform. Thus, the information of the specimen is obtained.

Stated another way, in this embodiment, the detection result of the first pixel at the time of detecting the first periodic pattern, the detection result of the second pixel at the time of detecting the first periodic pattern, and the detection result of the first pixel at the time of detecting the second periodic pattern are regarded as being originated from one periodic pattern (i.e., a composite periodic pattern). The information of the specimen is then derived by taking the Fourier transform of the composite periodic pattern.

The X-ray entering the first pixel at the time of detecting $I_5$ and the X-ray entering the first pixel at the time of detecting $I_6$ are the X-rays that have transmitted through the specimen at (substantially) the same position. Therefore, the information of the specimen given by the X-ray entering the first pixel at the time of detecting $I_5$ and the information of the specimen given by the X-ray entering the first pixel at the time of detecting $I_6$ are (substantially) the same.

On the other hand, a generally employed window function has larger amplitude at a position closer to a center. Accordingly, in trying to derive the wavefront information of the X-ray (light) entering $(x_0, y)$, a more accurate value is calculated when the detection result of the first pixel at the time of detecting $I_5$ and the detection result of the first pixel at the time of detecting $I_6$ are positioned closer to a center of the window function of the composite array I.

From that point of view, the detection result of the first pixel at the time of detecting $I_5$ and the detection result of the first pixel at the time of detecting $I_6$ are to be positioned close to each other. Because the distance between the detection result of the first pixel at the time of detecting $I_5$ and the detection result of the first pixel at the time of detecting $I_6$ within the composite moiré (i.e., the composite period pattern) is P−α, it is beneficial that P−α is smaller. More specifically, P−α is to be 3 or less.

When P−α is 3 or less, the detection result of the first pixel at the time of detecting $I_5$ and the detection result of the first pixel at the time of detecting $I_6$ are positioned within three pixels in the composite moiré I.

When P−α is 1, the detection results of the first pixel are adjacent to each other in the composite moiré I.

In this specification, the information of the specimen implies information obtained from the wavefront information of the X-ray (light) having transmitted through the specimen, e.g., information regarding absorption, scattering, and phase of the specimen. The wavefront information of the X-ray (light) at each of plural positions is derived by computing the wavefront information of the X-ray per the X-ray entering each pixel. Further, an absorption image, a scattering image, a differential phase image, and a phase image of the specimen are obtained by deriving plural pieces of information of the specimen from the wavefront information for each of plural positions, and mapping the derived information.

EXAMPLE 1

Example 1 will be described below in connection with a practical example in which a differential phase image in one direction is obtained with a simulation from a moiré having a period in one direction (i.e., a one-dimensional moiré) by using the wavefront measuring apparatus described in the first embodiment.

As in the first embodiment, the wavefront measuring apparatus used in EXAMPLE 1 is the wavefront measuring apparatus illustrated in FIG. 1. Details of the wavefront measuring apparatus are described below.

In EXAMPLE 1, a focal point of the X-ray source 110 is set to a size of 100 μm, and energy of the X-ray emitted from the X-ray source 110 is set to 17.5 keV.

Figure 4:
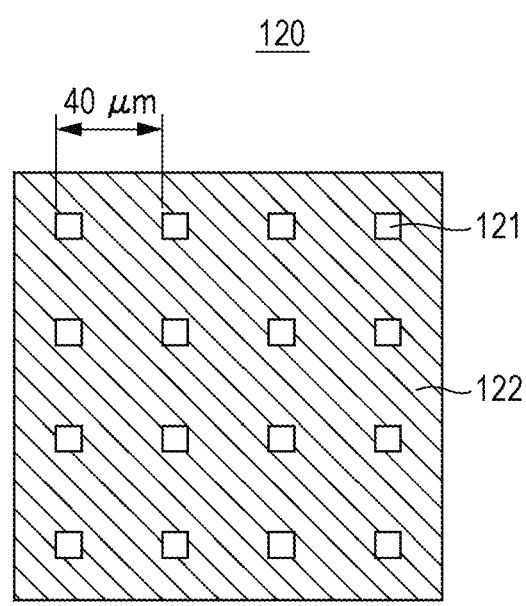
FIG. 4 is a schematic view of a source grating used in EXAMPLES 1 and 2.

FIG. 4 is a schematic view of the source grating 120 used in EXAMPLE 1. The source grating 120 used in EXAMPLE 1 is a two-dimensional grating in which a transmitting portion 121 and a shielding portion 122 are two-dimensionally arrayed. A grating period is set to 40 μm, and a width of each transmitting portion 121 is set to 5 μm.

Figure 5A:
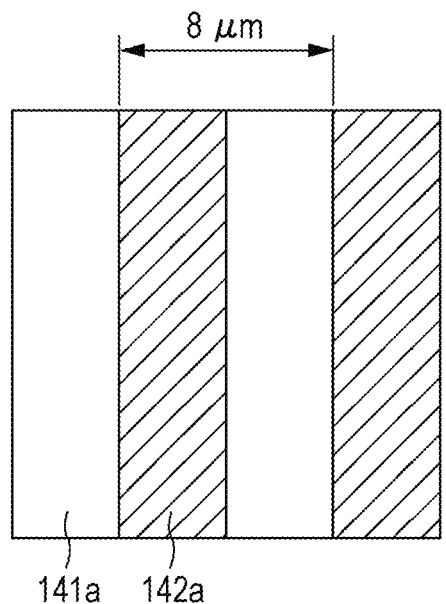
FIGS. 5A and 5B are schematic views of phase gratings used respectively in EXAMPLES 1 and 2.

FIG. 5A is a schematic view of a diffraction grating used in EXAMPLE 1. The diffraction grating used in EXAMPLE 1 is a one-dimensional phase grating 140a having a phase reference portion 141a and a phase shift portion 142a, which are arrayed at a period of 8 μm. The phase grating 140a is constructed such that a phase difference between an X-ray having transmitted through the phase reference portion 141a and an X-ray having transmitted through the phase shift portion 142a is π. That type of grating is called a π-grating.

Figure 6A:
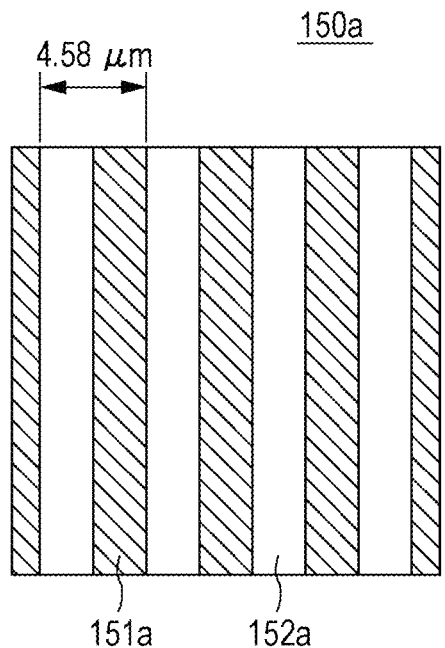
FIGS. 6A and 6B are schematic views of absorption gratings used respectively in EXAMPLES 1 and 2.

FIG. 6A is a schematic view of a shield grating 150a used in EXAMPLE 1. The shield grating 150a used in EXAMPLE 1 has a shielding portion 151a and a transmitting portion 152a, which are arrayed at a period of 4.58 μm. The shield grating 150a is arranged such that a distance between the phase grating 140a and the shield grating 150a is 1/10 of a distance between the source grating 120 and the phase grating 140a.

In the detector 160, pixels each having a size of 8×8 μm² and detecting the intensity of the X-ray are two-dimensionally arrayed to detect the X-ray from the shield grating 150a. A moiré formed by the phase grating 140a and the shield grating 150a has a period of 32 μm on the detector 160, and four pixels of the detector 160 correspond to one period of the moiré.

A specimen is prepared as four fibers each having a diameter of 250 μm and a complex refractive index of $6.70 \times 10^{-8} - i \times 9.07 \times 10^{-11}$.

An analytical method executed in EXAMPLE 1 by the computer is described below.

For convenience of explanation, a differential phase image of the specimen is obtained from two moirés $I_1$ and $I_2$ that are expressed by the following formulae (16):

$$I_1(x, y) = a(x, y) + b(x, y)\cos\left[2\pi\frac{1}{4}x + \varphi(x, y)\right] \tag{16}$$

$$I_2(x, y) = a(x, y) + b(x, y)\cos\left[2\pi\frac{1}{4}x + \varphi(x, y) + 2\pi\frac{2}{4}\right]$$

Given that m and n in the formula (7) are each +1, virtual moirés $I_3$ and $I_4$ are expressed by the following formulae (17) on the basis of the formula (16):

$$I_3(x, y) = I_1(x+1, y) \tag{17}$$
$$= a(x+1, y) + b(x+1, y)\cos\left[2\pi\frac{1}{4}(x+1) + \varphi(x+1, y)\right]$$
$$\approx a(x, y) + b(x, y)\cos\left[2\pi\frac{1}{4}(x+1) + \varphi(x, y)\right]$$

$$I_4(x, y) = I_2(x+1, y)$$
$$= a(x+1, y) + b(x+1, y)\cos\left[2\pi\frac{1}{4}(x+1) + \varphi(x+1, y) + 2\pi\frac{2}{4}\right]$$
$$\approx a(x, y) + b(x, y)\cos\left[2\pi\frac{1}{4}(x+1) + \varphi(x, y) + 2\pi\frac{2}{4}\right]$$

Figure 7A:
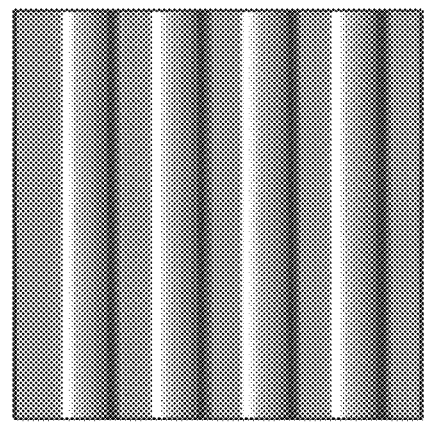
FIGS. 7A and 7B illustrate simulation results in EXAMPLE 1.
Figure 7B:
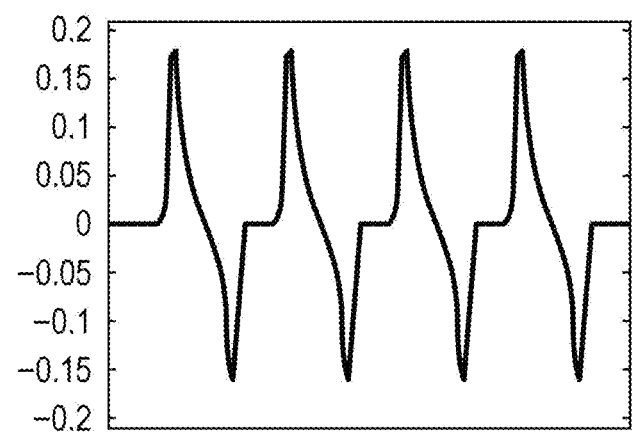

The differential phase image of the specimen is obtained by substituting the formulae (16) and (17) in the formula (11). FIG. 7A illustrates the differential phase image of the specimen obtained in EXAMPLE 1, and FIG. 7B illustrates a line profile of the differential phase image illustrated in FIG. 7A.

Comparative Example 1

COMPARATIVE EXAMPLE 1 will be described below in connection with an example in which a differential phase image of a specimen is obtained by using the phase shifting method.

A simulation is performed by using the same specimen as in EXAMPLE 1 on condition that a wavefront measuring apparatus used in COMPARATIVE EXAMPLE 1 is the same as in EXAMPLE 1 except for a computer.

An analytical method executed by the computer in COMPARATIVE EXAMPLE 1 is described below.

In COMPARATIVE EXAMPLE 1, the differential phase image is obtained from four moirés, which are expressed by the following formulae (18), and the formula (3):

$$I_7(x, y) = a(x, y) + b(x, y)\cos\left[2\pi\frac{1}{4}x + \varphi(x, y)\right] \tag{18}$$

$$I_8(x, y) = a(x, y) + b(x, y)\cos\left[2\pi\frac{1}{4}x + \varphi(x, y) + 2\pi\frac{1}{4}\right]$$

$$I_9(x, y) = a(x, y) + b(x, y)\cos\left[2\pi\frac{1}{4}x + \varphi(x, y) + 2\pi\frac{2}{4}\right]$$

$$I_{10}(x, y) = a(x, y) + b(x, y)\cos\left[2\pi\frac{1}{4}x + \varphi(x, y) + 2\pi\frac{3}{4}\right]$$

Figure 20A:
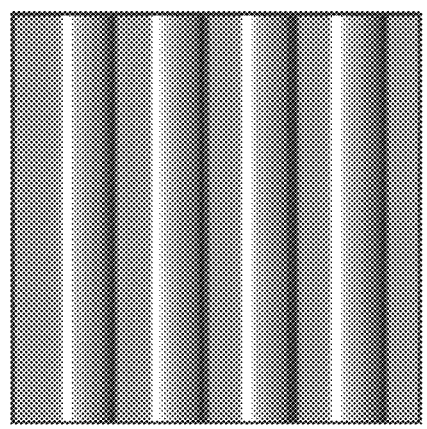
FIGS. 20A and 20B illustrate simulation results in COMPARATIVE EXAMPLE 1.
Figure 20B:
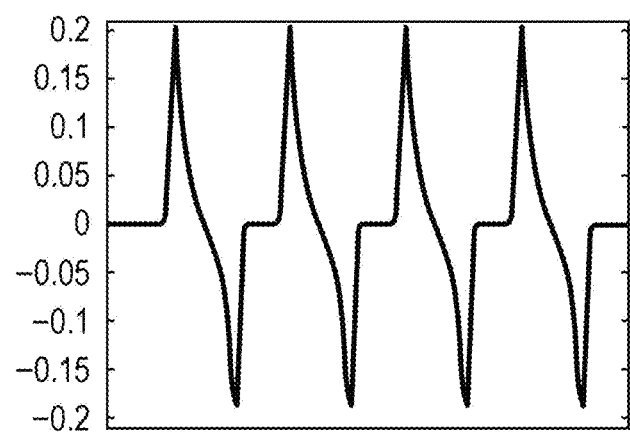

FIG. 20A illustrates the differential phase image of the specimen obtained in COMPARATIVE EXAMPLE 1, and FIG. 20B illustrates a line profile of the differential phase image illustrated in FIG. 20A.

While the information of the specimen is obtained in COMPARATIVE EXAMPLE 1 from four moirés independently for each pixel, the information of the specimen is obtained in EXAMPLE 1 from two moirés by using the detection result of each pixel and another pixel adjacent to the relevant pixel. Thus, while the phase shifting method employs at least three moirés, the information of the specimen is obtained from two moirés in EXAMPLE 1.

Comparative Example 2

COMPARATIVE EXAMPLE 2 will be described below in connection with an example in which a differential phase image of a specimen is obtained by using the windowed Fourier transform method.

A simulation is performed by using the same specimen as in EXAMPLE 1 on condition that a wavefront measuring apparatus used in COMPARATIVE EXAMPLE 2 is also the same as in EXAMPLE 1 except for a computer.

An analytical method executed by the computer in COMPARATIVE EXAMPLE 2 is described below.

In COMPARATIVE EXAMPLE 2, $I_7$, which is expressed as one of the formulae (18), and the formulae (5) are used. Further, a Gauss function is used as the window function. Because spectra of a(x, y), c(x, y) and c*(x, y) expressed by the formulae (5) are overlapped with each other in a wavenumber space, those spectra are processed to be separated from one another.

Figure 21A:
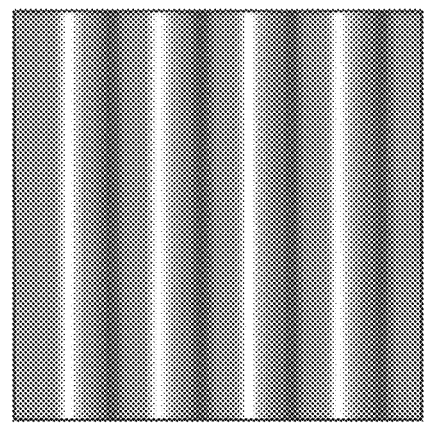
FIGS. 21A and 21B illustrate simulation results in COMPARATIVE EXAMPLE 2.
Figure 21B:
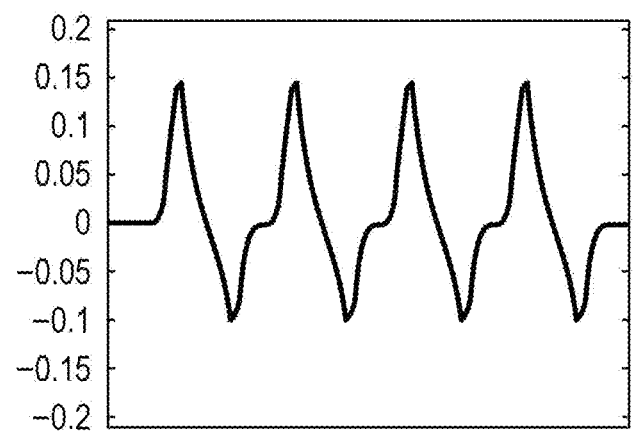

FIG. 21A illustrates the differential phase image obtained in COMPARATIVE EXAMPLE 2, and FIG. 21B illustrates a line profile of the differential phase image illustrated in FIG. 21A. Comparing FIGS. 7A and 7B (EXAMPLE 1) and FIGS. 21A and 21B (COMPARATIVE EXAMPLE 2) with FIGS. 20A and 20B (COMPARATIVE EXAMPLE 1), the differential phase image closer to that in COMPARATIVE EXAMPLE 1 is obtained in EXAMPLE 1 than in COM- PARATIVE EXAMPLE 2. It is hence considered that the differential phase image of the specimen obtained in EXAMPLE 1 is closer to the exact one than that obtained in COMPARATIVE EXAMPLE 2.

EXAMPLE 2

EXAMPLE 2 will be described below in connection with a practical example in which a differential phase image in an x-direction and a differential phase image in a y-direction are obtained with a simulation from a moiré (two-dimensional moiré) having periods in two directions, i.e., the x-direction and the y-direction, by using the wavefront measuring apparatus described in the first embodiment. When the differential phase image in the x-direction and the differential phase image in the y-direction are computed from the two-dimensional moiré, computations may also be executed for the two directions in a similar manner to the case of the one-dimensional moiré. Hence duplication descriptions of similar points to those in EXAMPLE 1 are omitted.

An X-ray source 110, a source grating 120, and a detector 160, used in EXAMPLE 2, are the same as those used in EXAMPLE 1.

Figure 5B:
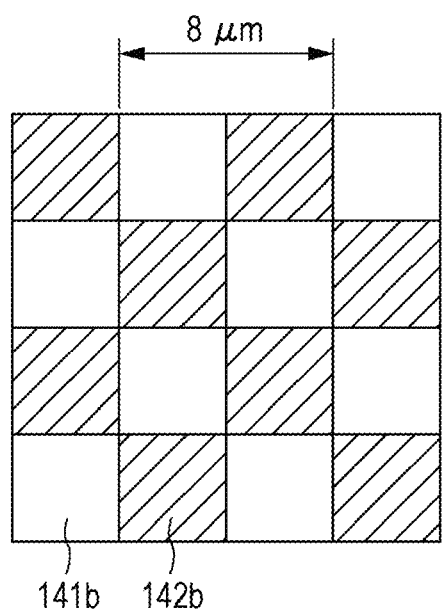

FIG. 5B is a schematic view of a diffraction grating used in EXAMPLE 2. The diffraction grating used in EXAMPLE 2 is a two-dimensional phase grating 140b having a phase reference portion 141b and a phase shift portion 142b, which are two-dimensionally arrayed at a period of 8 μm. As in EXAMPLE 1, the phase grating 140b is a π-grating.

Figure 6B:
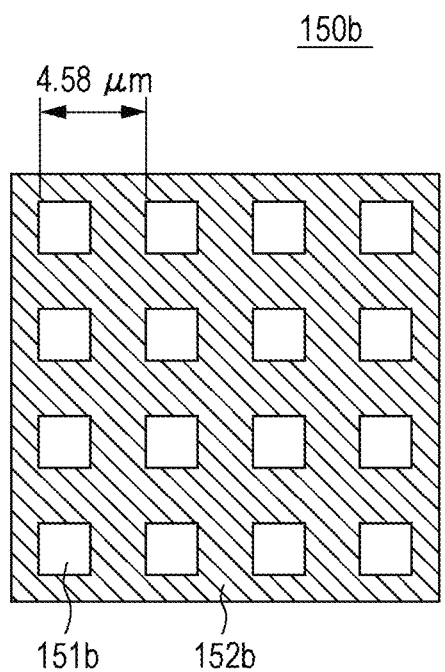

FIG. 6B is a schematic view of a shield grating 150b used in EXAMPLE 2. The shield grating 150b used in EXAMPLE 2 has a shielding portion 151b and a transmitting portion 152b, which are two-dimensionally arrayed at a period of 4.58 μm. Further, as in EXAMPLE 1, the shield grating 150b is arranged such that a distance between the phase grating 140b and the shield grating 150b is ⅒ of a distance between the source grating 120 and the phase grating 140b.

A specimen is a sphere having a diameter of 800 μm and a complex refractive index of $7.77 \times 10^{-8} - i \times 9.42 \times 10^{-11}$.

In EXAMPLE 2, the differential phase image in the x-direction is obtained by employing a reference moiré (first photoperiod pattern) and a moiré (second photoperiod pattern) having a phase shifted by π in the x-direction from the reference moiré. Further, the differential phase image in the y-direction is obtained by employing the reference moiré (first photoperiod pattern) and a moiré (third photoperiod pattern) having a phase shifted by π in the y-direction from the reference moiré. In other words, the differential phase images in the x-direction and the y-direction are obtained from three moirés in total. Here, as a matter of course, a phase shift direction (x-direction) of the second photoperiod pattern with respect to the first photoperiod pattern is perpendicular to a phase shift direction (y-direction) of the third photoperiod pattern with respect to the first photoperiod pattern. A manner of computing the differential phase image in each of the x-direction and the y-direction is described in brief below although it is similar to that in EXAMPLE 1.

To explain an analytical method used in EXAMPLE 2, a pixel where the X-ray intensity at (x, y) is detected is defined as a first pixel, a pixel where the X-ray intensity at (x−m, y) is detected is defined as a second pixel, and a pixel where the X-ray intensity at (x, y−q) is detected is defined as a third pixel.

In EXAMPLE 2, the differential phase image in the x-direction is computed by using detection results of the first pixel and the second pixel at the time of detecting the first photoperiod pattern and detection results of the first pixel and the second pixel at the time of detecting the second photoperiod pattern.

Further, the differential phase image in the y-direction is computed by using detection results of the first pixel and the third pixel at the time of detecting the first photoperiod pattern and detection results of the first pixel and the third pixel at the time of detecting the third photoperiod pattern.

Figure 8A:
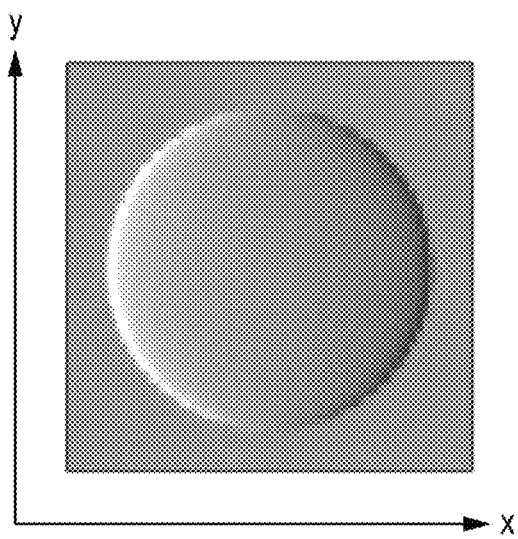
FIGS. 8A and 8B illustrate simulation results in EXAMPLE 2.
Figure 8B:
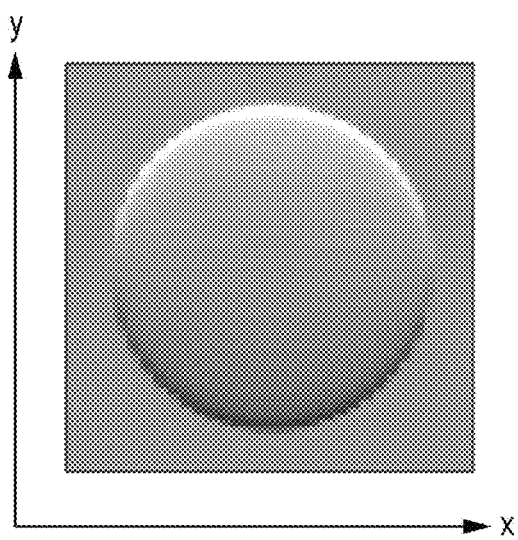

FIG. 8A illustrates the differential phase image in the x-direction, which is obtained by using the first photoperiod pattern and the second photoperiod pattern. FIG. 8B illustrates the differential phase image in the y-direction, which is obtained by using the first photoperiod pattern and the third photoperiod pattern. Thus, in EXAMPLE 3, the two-dimensional differential phase image is obtained from three moirés.

Comparative Example 3

COMPARATIVE EXAMPLE 3 will be described below in connection with an example in which a two-dimensional differential phase image of a specimen is obtained by using the phase shifting method.

A simulation is performed by using the same specimen as in EXAMPLE 2 on condition that a wavefront measuring apparatus used in COMPARATIVE EXAMPLE 3 is the same as in EXAMPLE 2 except for a computer.

An analytical method executed by the computer in COMPARATIVE EXAMPLE 3 is described below.

In COMPARATIVE EXAMPLE 3, the differential phase image in the x-direction is obtained from four moirés, of which phases are shifted in units of 0.5π in the x-direction, by using the formula (3). Similarly, the differential phase image in the y-direction is obtained from four moirés, of which phases are shifted in units of 0.5π in the y-direction, by using the formula (3). Thus, the two-dimensional differential phase image is obtained from seven moirés in total.

Figure 22A:
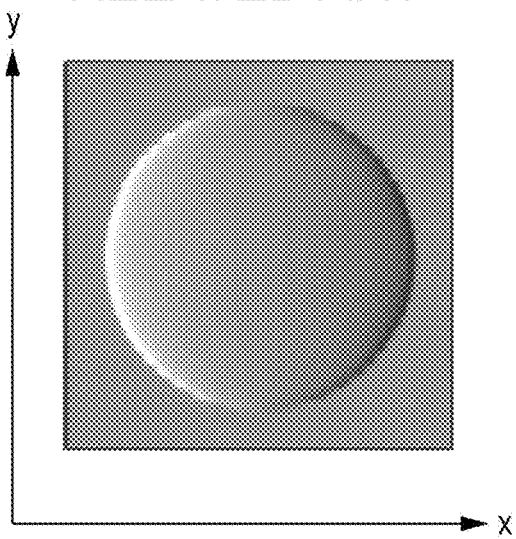
FIGS. 22A and 22B illustrate simulation results in COMPARATIVE EXAMPLE 3.
Figure 22B:
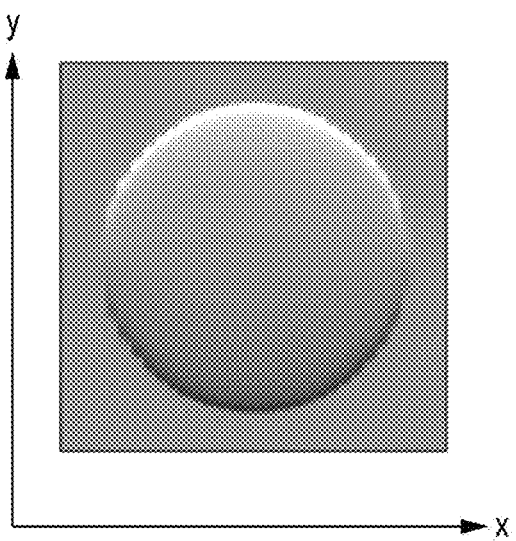

FIGS. 22A and 22B illustrate the differential phase images in the x-direction and the y-direction, respectively, which are obtained in COMPARATIVE EXAMPLE 3. It is to be noted that five or more moirés are used when the two-dimensional differential phase image is obtained by using the phase shifting method.

Comparative Example 4

COMPARATIVE EXAMPLE 4 will be described below in connection with an example in which a two-dimensional differential phase image of a specimen is obtained by using the windowed Fourier transform method. A simulation is also performed by using the same specimen as in EXAMPLE 2 on condition that a wavefront measuring apparatus used in COMPARATIVE EXAMPLE 4 is the same as in EXAMPLE 2 except for a computer.

An analytical method executed by the computer in COMPARATIVE EXAMPLE 4 is described below.

In COMPARATIVE EXAMPLE 4, the differential phase images in the x-direction and the y-direction are obtained from one moiré by using the formulae (5). Further, a Gauss function is used as the window function. Because spectra of $a(x, y)$, $c(x, y)$ and $c^*(x, y)$ are overlapped with each other in a wavenumber space, those spectra are processed to be separated from one another.

Figure 23A:
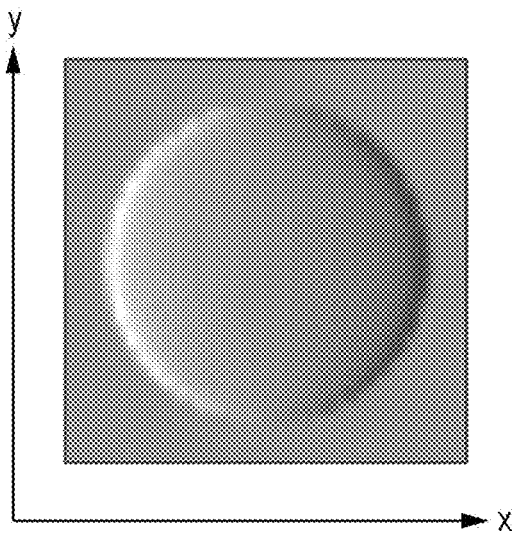
FIGS. 23A and 23B illustrate simulation results in COMPARATIVE EXAMPLE 4.
Figure 23B:
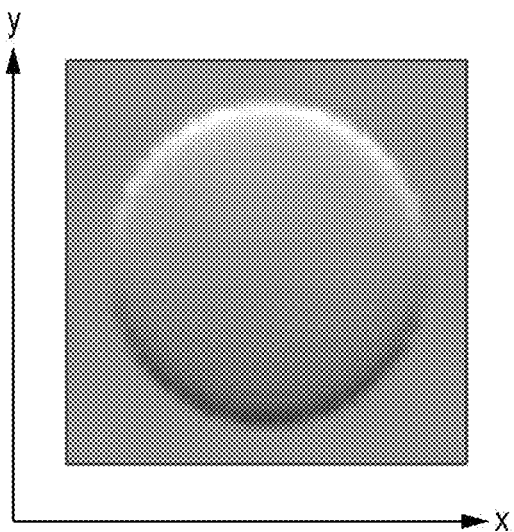

FIGS. 23A and 23B illustrate the differential phase images in the x-direction and the y-direction, respectively, which are obtained in COMPARATIVE EXAMPLE 4.

Figure 9A:
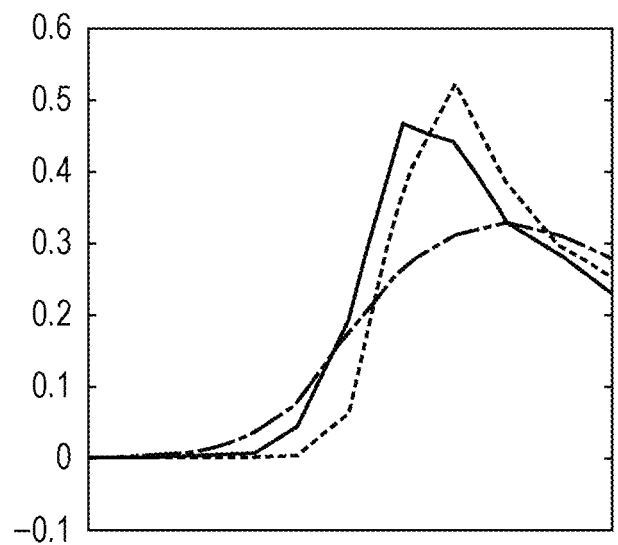
FIGS. 9A and 9B each illustrate line profiles as simulation results in EXAMPLE 2 and COMPARATIVE EXAMPLES 3 and 4.
Figure 9B:
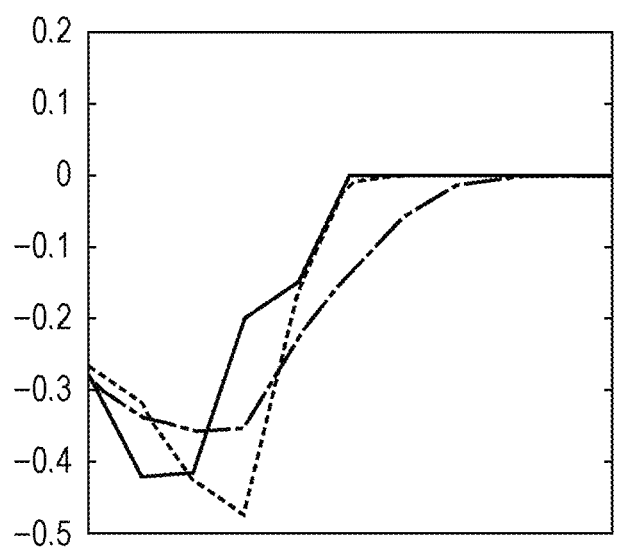

FIGS. 9A and 9B illustrate line profiles formed by using the differential phase images of the specimen in the x-direction, which are obtained in EXAMPLE 2 and COMPARATIVE EXAMPLES 3 and 4. FIG. 9A illustrates line profiles of a left end of the specimen, and FIG. 9B illustrates line profiles of a right end of the specimen. Among three lines in each of FIGS. 9A and 9B, a solid line represents the line profile of the differential phase image obtained in EXAMPLE 2, a dotted line represents the line profile of the differential phase image obtained in COMPARATIVE EXAMPLE 3, and a one-dot-chain line represents the line profile of the differential phase image obtained in COMPARATIVE EXAMPLE 4. As seen from FIGS. 9A and 9B, the result obtained in EXAMPLE 2 is closer to the result obtained in COMPARATIVE EXAMPLE 3 than in COMPARATIVE EXAMPLE 4. It is hence considered that a more accurate differential phase image is obtained in EXAMPLE 2 than in COMPARATIVE EXAMPLE 4.

EXAMPLE 3

EXAMPLE 3 will be described below in connection with a practical example in which a one-dimensional differential phase image (i.e., an image resulting from differentiating a phase image in one direction) is obtained with a simulation from a moiré having a period in one direction (i.e., a one-dimensional moiré) by using a wavefront measuring apparatus that executes the analytical method described in the second embodiment.

The wavefront measuring apparatus used in EXAMPLE 3 is the same as in EXAMPLE 1 except for a computer, and a specimen used in EXAMPLE 3 is also the same as in EXAMPLE 1.

A method of analyzing a moiré by the computer in EXAMPLE 3 is described below.

In EXAMPLE 3, a differential phase image of a specimen is obtained from a reference moiré $I_5$ and a moiré $I_6$ having a phase shifted by $0.5\pi$ with respect to the reference moiré $I_5$. The following formulae (19) are obtained by substituting a moiré period P=4, which is in units of pixel size of the detector, and $\alpha=1$ in the formulae (13).

$$I(x, y) = \begin{cases} I_5(x, y), & \text{for } x \le x_0 + 1 \\ I_6(x-1, y), & \text{for } x \ge x_0 + 2 \end{cases} \quad (19)$$

Figure 10A:
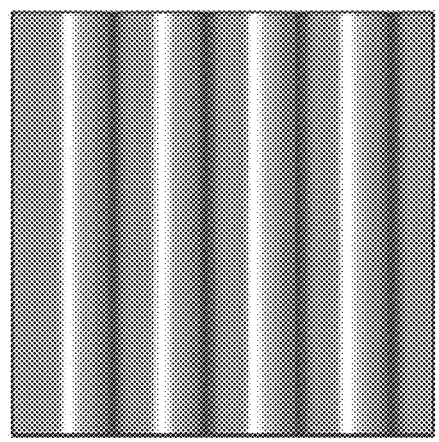
FIGS. 10A and 10B illustrate simulation results in EXAMPLE 3.
Figure 10B:
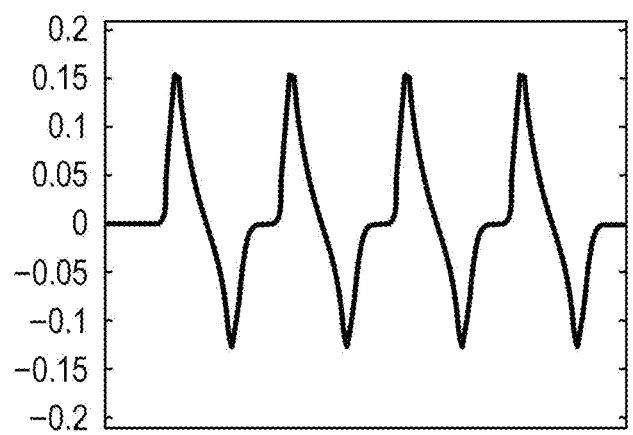

The differential phase image is obtained by analyzing the moiré, expressed by the formulae (19), in accordance with the formula (5). FIGS. 10A and 10B illustrate respectively the differential phase image and a line profile of the specimen, which are obtained in EXAMPLE 3. Comparing FIGS. 10A and 10B (EXAMPLE 3) and FIGS. 21A and 21B (COMPARATIVE EXAMPLE 2) with FIGS. 20A and 20B (COMPARATIVE EXAMPLE 1), the result closer to that in COMPARATIVE EXAMPLE 1 is obtained in EXAMPLE 3 than in COMPARATIVE EXAMPLE 2. It is hence considered that the differential phase image obtained in EXAMPLE 3 is closer to the exact one than that obtained in COMPARATIVE EXAMPLE 2.

EXAMPLE 4

EXAMPLE 4 will be described below in connection with a practical example in which a differential phase image in the x-direction and a differential phase image in the y-direction are obtained with a simulation from a two-dimensional moiré by using a wavefront measuring apparatus that executes the analytical method described in the second embodiment.

The wavefront measuring apparatus used in EXAMPLE 4 is the same as in EXAMPLE 2 except for a computer, and a specimen used in EXAMPLE 4 is also the same as in EXAMPLE 2.

A method of analyzing a moiré by the computer in EXAMPLE 4 is described below.

In EXAMPLE 4, the differential phase image in the x-direction is obtained from a reference moiré and a moiré having a phase shifted by $0.25\pi$ in the x-direction with respect to the reference moiré by using the formulae (13) and (5). Similarly, the differential phase image in the y-direction is obtained from a reference moiré and a moiré having a phase shifted by $0.25\pi$ in the y-direction with respect to the reference moiré by using the formulae (13) and (5). Additionally, P=4 and $\alpha=1$ are set.

Thus, in EXAMPLE 4, the differential phase images of the specimen in the x-direction and the y-direction are obtained from three moirés in total.

Figure 11A:
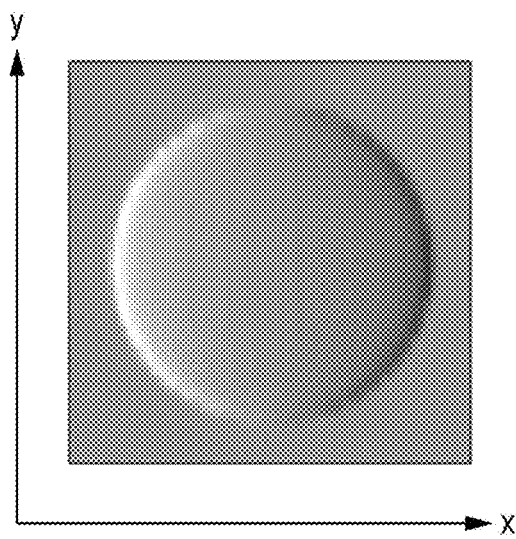
FIGS. 11A and 11B illustrate simulation results in EXAMPLE 4.
Figure 11B:
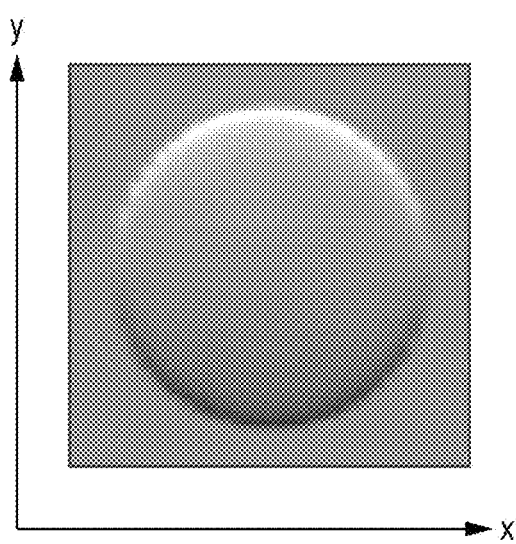
Figure 12A:
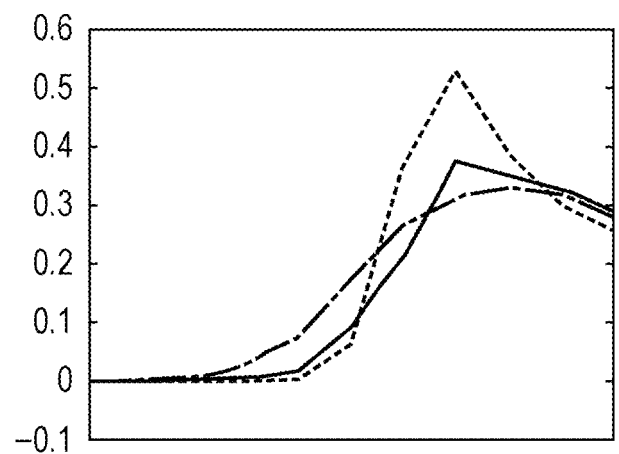
FIGS. 12A and 12B each illustrate line profiles as simulation results in EXAMPLE 4 and COMPARATIVE EXAMPLES 3 and 4.
Figure 12B:
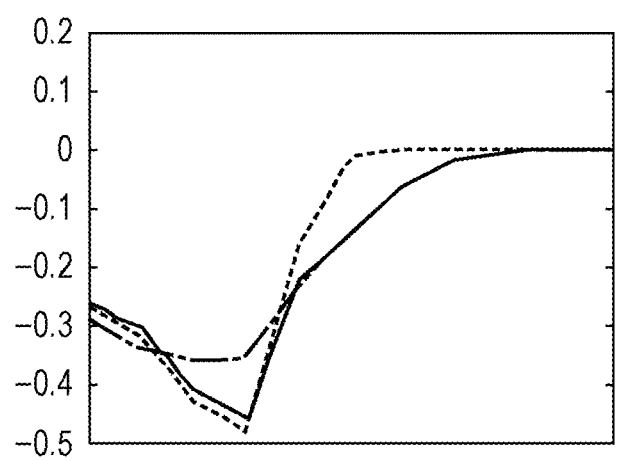

FIG. 11A illustrates the differential phase image in the x-direction obtained in EXAMPLE 4, and FIG. 11B illustrates the differential phase image in the y-direction obtained in EXAMPLE 4. Further, line profiles are formed by using the differential phase images of the specimen in the x-direction, which are obtained in EXAMPLE 4 and COMPARATIVE EXAMPLES 3 and 4. FIG. 12A illustrates line profiles of a left end of the specimen, and FIG. 12B illustrates line profiles of a right end of the specimen. Among three lines in each of FIGS. 12A and 12B, a solid line represents the line profile of the differential phase image obtained in EXAMPLE 4, a dotted line represents the line profile of the differential phase image obtained in COMPARATIVE EXAMPLE 3, and a one-dot-chain line represents the line profile of the differential phase image obtained in COMPARATIVE EXAMPLE 4. As seen from FIGS. 12A and 12B, the result obtained in EXAMPLE 4 is closer to the result obtained in COMPARATIVE EXAMPLE 3 than in COMPARATIVE EXAMPLE 4. It is hence considered that a more accurate differential phase image is obtained in EXAMPLE 4 than in COMPARATIVE EXAMPLE 4.

While the foregoing description has been made in connection with the case where the present disclosure is applied to an interferometer carrying out a differential interference method, application fields of the present disclosure are not limited to the interferometer carrying out the differential interference method. The present disclosure may also be applied to not only an interferometer carrying out an interference method (other than the differential one), but also to a wavefront measuring apparatus not utilizing interference.

EXAMPLE 5

EXAMPLE 5 will be briefly described below by referring to FIG. 13 in connection with the case where the present disclosure is applied to a wavefront measuring apparatus, which is described in PCT Japanese Translation Patent Publication No. 2010-502977, as an example of the wavefront measuring apparatus not utilizing interference.

Figure 13:
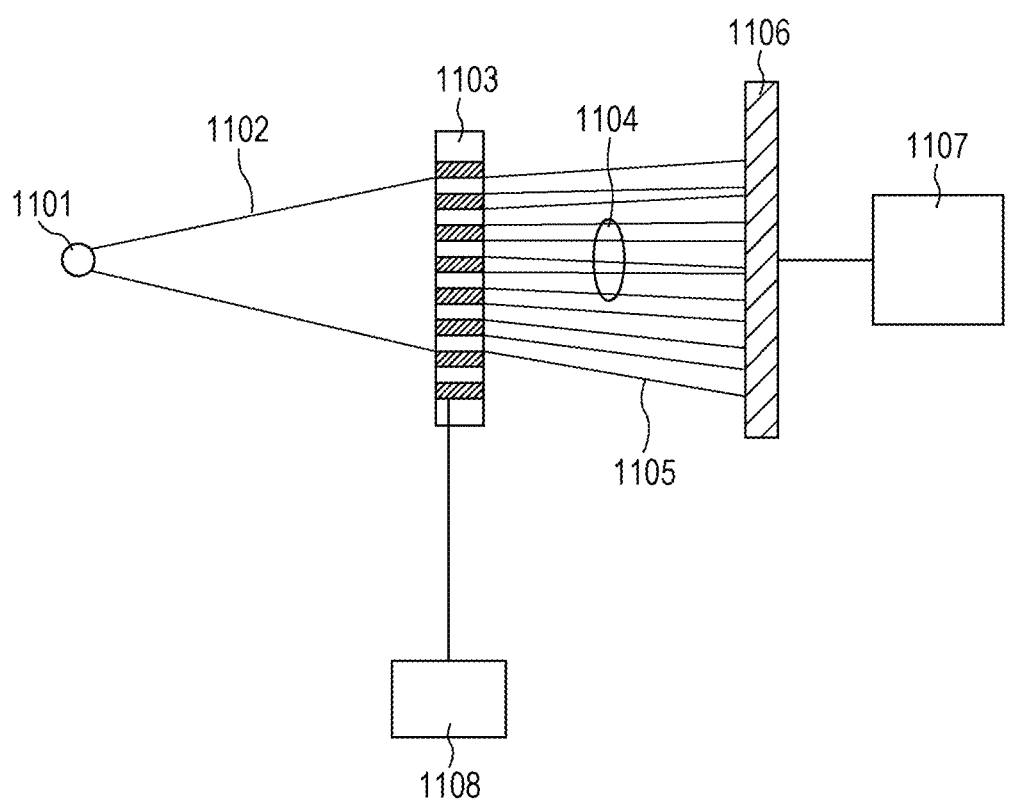
FIG. 13 is an overall view of a wavefront measuring apparatus used in EXAMPLE 5.

In a wavefront measuring apparatus 1000 of FIG. 13, information regarding a phase of a specimen is obtained by delivering an X-ray to a specimen, detecting and analyzing an amount by which the X-ray is refracted by the specimen, and deriving wavefront information.

The wavefront measuring apparatus 1000 illustrated in FIG. 13 includes an X-ray source 1101, a division element 1103 for dividing a divergent X-ray 1102 emitted from the X-ray source 1101 to form plural X-ray beams 1105, and a detector 1106 for detecting the X-ray beams 1105. The wavefront measuring apparatus 1000 further includes a computer 1107 as an arithmetic unit for executing calculations based on a detection result of a periodic pattern by the detector 1106, and an actuator 1108 that serves as a moving unit to move the division element 1103. A specimen 1104 may be positioned between the division element 1103 and the detector 1106, as illustrated in FIG. 13. Alternatively, the specimen 1104 may be positioned between the X-ray source 1101 and the division element 1103.

In the wavefront measuring apparatus 1000 illustrated in FIG. 13, a periodic pattern corresponding to a difference of the X-ray intensity is formed on the detector 1106 because the emitted X-ray 1102 is divided by the division element 1103. Further, a phase of the periodic pattern is shifted because the division element 1103 is moved by the actuator 1108. It is, therefore, possible to detect a first periodic pattern by the detector 1106, and then to obtain a second periodic pattern by performing the detection again after moving the division element 1103 with the actuator 1108. A method of deriving wavefront information by using the first periodic pattern and the second periodic pattern is similar to the above-described method of deriving the wavefront information by using the first periodic pattern and the second periodic pattern, which are obtained with the shearing interferometer. Hence description of the method of deriving the wavefront information is omitted.

EXAMPLE 6

EXAMPLE 6 will be described below in connection with an example of an X-ray computed tomography apparatus (X-ray CT apparatus) in which a tomographic image is obtained from projection images taken of a specimen from all-around directions. The X-ray CT apparatus of EXAMPLE 6 is also one type of wavefront measuring apparatus. In EXAMPLE 6, a tomographic phase image is obtained by using, as a projection phase image, the differential phase image obtained with the wavefront measuring method that is executed in the wavefront measuring apparatus of the first embodiment.

Figure 15:
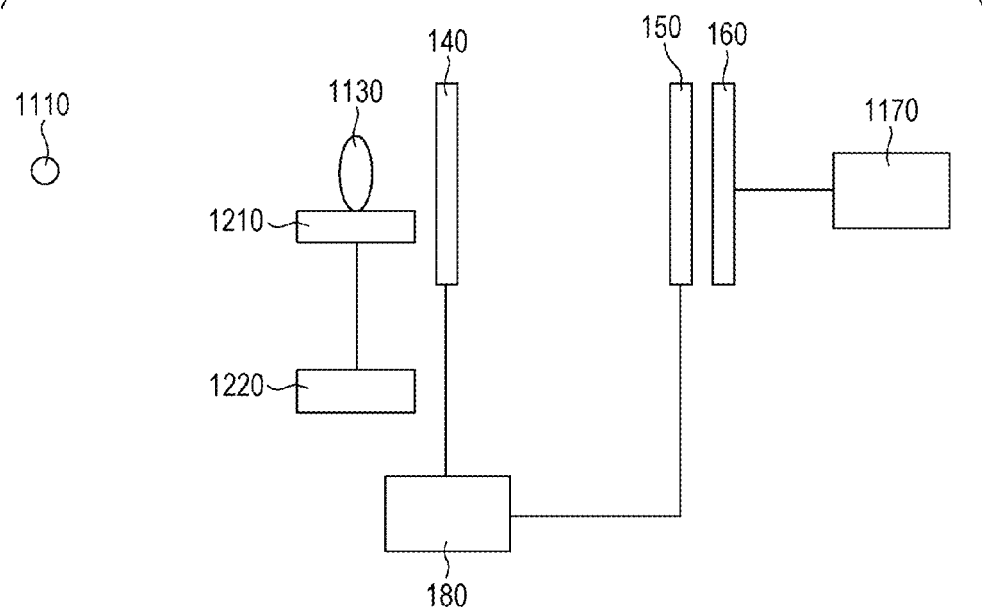
FIG. 15 is an overall view of a wavefront measuring apparatus used in each of EXAMPLES 6 and 7.

FIG. 15 illustrates a wavefront measuring apparatus 101 of EXAMPLE 6. The wavefront measuring apparatus 101 includes, as a light source, an X-ray source 1110 emitting a parallel X-ray (parallel light), but it does not include a source grating. The wavefront measuring apparatus 101 further includes a table 1210 on which a specimen 1130 is placed, and an actuator 1220 for moving the table 1210. Moreover, the wavefront measuring apparatus 101 differs from the wavefront measuring apparatus 1, illustrated in FIG. 1, in that information of a tomographic image is derived by a computer 1170, which executes calculations based on detection results by a detector 160.

On the other hand, the wavefront measuring apparatus 101 is similar to the wavefront measuring apparatus 1, illustrated in FIG. 1, in that an interference pattern is formed by a phase grating 140, that a shield grating 150 is arranged at a position where the interference pattern is formed, thereby forming a moiré, and that the moiré is detected by the detector 160.

While the wavefront measuring apparatus 101 is constructed such that the specimen is rotated by a combination of the table 1210 and the actuator 1220 for rotating the table 1210, the wavefront measuring apparatus 101 may be rotated instead of rotating the specimen. Plural projection images are obtained by taking images of a wavefront, which has been modulated in phase by the specimen, at plural projection angles, and a tomographic image of the specimen is obtained from the plural projection images.

Figure 16A:
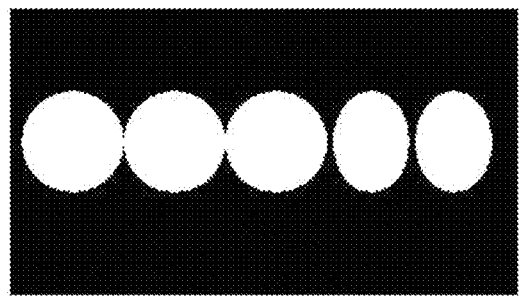
FIGS. 16A to 16D illustrate a specimen used in EXAMPLES 6 and 7.
Figure 16B:
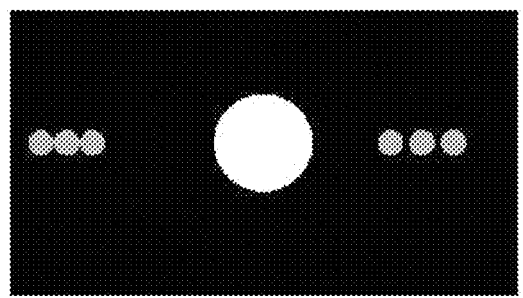
Figure 16C:
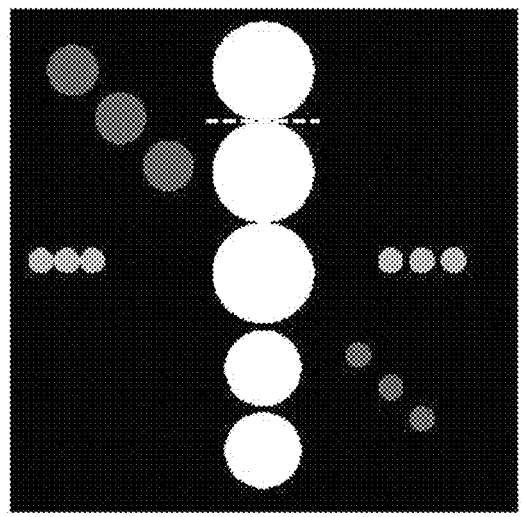
Figure 16D:
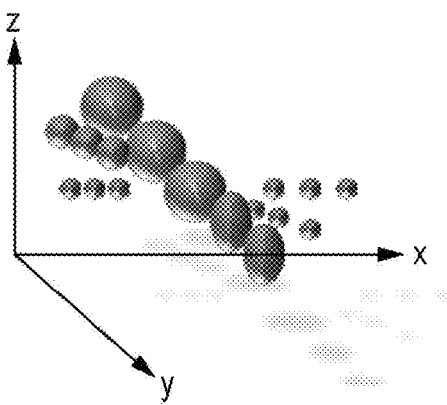
Figure 17A:
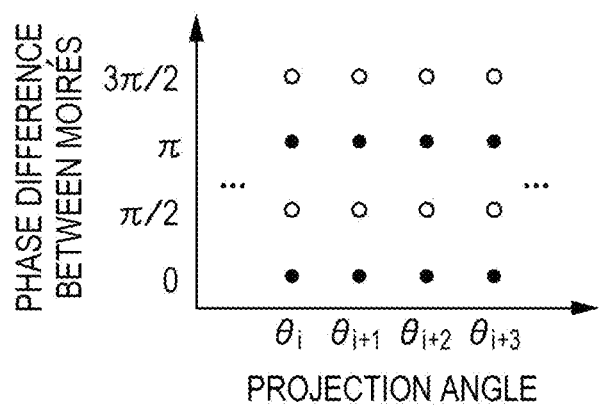
FIGS. 17A to 17C illustrate a moiré acquisition manner and a simulation result in EXAMPLE 6.

FIGS. 16A to 16D illustrate the specimen 1130 used in EXAMPLE 6. FIG. 16A is a sectional view of the specimen cut along a yz-plane, and FIG. 16B is a sectional view of the specimen cut along an xz-plane. FIG. 16C is a sectional view of the specimen cut along an xy-plane, and FIG. 16D is a perspective view of the specimen. In EXAMPLE 6, the specimen is rotated through 180 degrees in units of 1.40625 degrees, and images of the specimen are taken from 128 directions. At each projection angle, a reference moiré and a moiré, which has a phase shifted by $\pi$ in an X-direction (defined as a direction perpendicular to both the rotation axis of the specimen and the projection direction) with respect to the reference moiré, are detected. FIG. 17A illustrates the concept of detecting the moirés at each projection angle. In FIG. 17A, the horizontal axis represents a projection angle, and the vertical axis represents a phase difference in the X-direction with respect to the reference moiré. The moiré is detected at each of positions of the projection angle and the phase difference, which are indicated by black circles (●) in FIG. 17A, while the moiré is not detected at each of positions of the projection angle and the phase difference, which are indicated by white circles (○) in FIG. 17A. However, the positions of the projection angle and the phase difference at each of which the moiré is to be detected are not limited to those ones illustrated in FIG. 17A. As another example, the moiré may be detected at positions indicated by black circles in FIG. 17C. In other words, when the tomographic phase image is obtained from the differential phase image as in EXAMPLE 6, the phase differences of the detected moirés with respect to the reference moiré may be not the same at all the projection angles because it is just enough that the differential phase image of the specimen is obtained at each projection angle.

A projection differential phase image in the X-direction at each projection angle is obtained from the detected moirés in a similar method to that used in obtaining the differential phase image in EXAMPLE 1. More specifically, projection differential phase images in 128 directions are obtained from 256 moirés. Further, the tomographic phase image of the specimen is obtained from the projection differential phase images in those 128 directions. A method of obtaining the tomographic phase image from the projection differential phase images is described below.

In EXAMPLE 6, a Filtered Back Projection (FBP) method is used as an image reconstruction method for obtaining the tomographic phase image from the differential phase images. Because the FBP method is widely known as one of image reconstruction methods, outline of the FBP method is described below. It is, however, to be noted that the method of obtaining the tomographic phase image from the differential phase images is not limited to the FBP method and various image reconstruction methods may be optionally used.

Generally speaking, the image reconstruction method is a technique of obtaining a distribution of a two- or three-dimensional physical value of an object from projection images taken of the object from all-around directions. In other words, the ordinary image reconstruction method is a technique of obtaining a three-dimensional distribution $f(x, y, z)$ of a physical value of a specimen from a projection $\int f(x, y, z)ds$ (ds is a line element along the projection direction) of the specimen. While only the image reconstruction method for obtaining a distribution of a physical value in each cross-section (i.e., a plane defined by each projection direction) of an object is discussed in EXAMPLE 6, the present disclosure is not limited to such an application field.

Figure 14A:
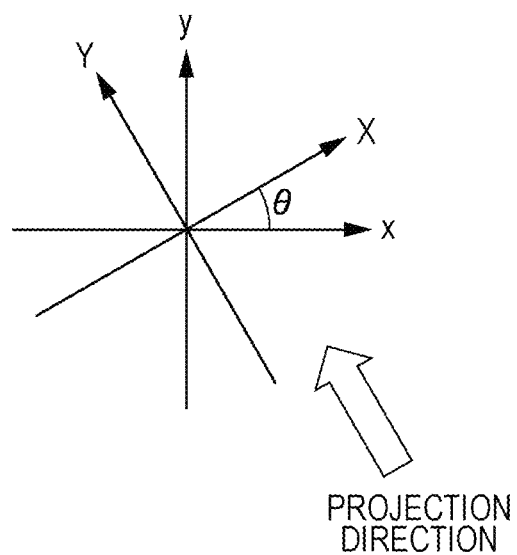
FIGS. 14A and 14B are illustrations to explain definition of coordinate axes.
Figure 14B:
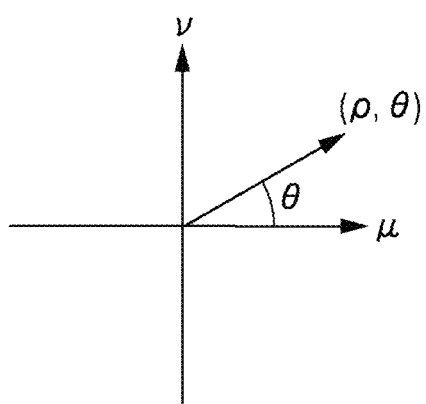

The FBP method of obtaining a distribution (also called a tomographic image) $f(x, y)$ of a physical value of an object in each cross-section from projection images is described in more detail. Definition of an x-axis and a y-axis is described with reference to FIG. 14A. As illustrated in FIG. 14A, the x-axis and the y-axis are defined in a plane containing the projection direction that is denoted by an arrow. Although a z-axis is defined perpendicularly to both the x-axis and the y-axis, the z-axis is not illustrated for simplicity. It is to be noted that the definition of the axes in EXAMPLE 6 differs from that in the above-described EXAMPLE 5 and others. As illustrated in FIG. 14A, a coordinate system obtained by rotating an x-y coordinate system by θ is defined as an X-Y coordinate system. FIG. 14B illustrates a frequency space resulting from transforming a space (real space) illustrated in FIG. 14A. A coordinate system of the (spatial) frequency space corresponding to the x-y coordinate system is defined as a μ-ν coordinate system.

First, a projection image p(X, θ) is defined by the following formula (20):

$$p(X,\theta)=\int_{-\infty}^{\infty} f(X,Y)dY \quad (20)$$

Next, a two-dimensional Fourier spectrum F(μ, ν) of f(x, y) is considered. The spectrum F(μ, ν) is expressed by the following formula (21):

$$F(\mu,\nu)=\int_{-\infty}^{\infty}\int_{-\infty}^{\infty} f(x,y)\exp[-i(\mu x+\nu y)]dxdy \quad (21)$$

Based on polar coordinate representation (ρ, θ), the formula (21) is rewritten into:

$$F(\mu, \nu) = \int_{-\infty}^{\infty}\int_{-\infty}^{\infty} f(X, Y)\exp[-i\rho X]dXdY \quad (22)$$
$$= \int_{-\infty}^{\infty} p(X, \theta)\exp[-i\rho X]dX$$
$$\equiv \mathcal{F}_{(X)}[p(X, \theta)]$$

where $F_{(x)}[a]$ denotes Fourier transform of a in the X-direction. Furthermore, the following relationship is employed:

$$\begin{pmatrix}\mu\\\nu\end{pmatrix}=\rho\begin{pmatrix}\cos\theta\\\sin\theta\end{pmatrix} \quad (23)$$
$$\begin{pmatrix}X\\Y\end{pmatrix}=\begin{pmatrix}\cos\theta & \sin\theta\\-\sin\theta & \cos\theta\end{pmatrix}\begin{pmatrix}x\\y\end{pmatrix}$$

The formula (22) implies that a spectrum obtained with one-dimensional Fourier transform of p(X, θ) in the X-direction is equal to a spectrum of spectrum F(μ, ν) in the O-direction. The formula (22) is known as the projection slice theorem.

Accordingly, f(x, y) is obtained by taking two-dimensional inverse Fourier transform of F(μ, ν), as expressed by the following formula (24):

$$f(x,y)=\int_{-\infty}^{\infty}\int_{-\infty}^{\infty} F(\mu,\nu)\exp[i(\mu x+\nu y)]d\mu d\nu \quad (24)$$

The formula (24) is rewritten to the following formula (25) by using the formula (22):

$$f(x,y)=\int_{-\infty}^{\infty}\int_{0}^{\pi} \mathcal{F}_{(X)}[p(X,\theta)]|\rho|\exp[i\rho x]d\rho d\theta \quad (25)$$

Thus, it is understood from the formula (25) that the tomographic image is obtained from the projection image through the following operations:

(i) Take Fourier transform of each projection image p(X, θ).

(ii) Multiply a frequency filter |ρ| by the obtained spectrum $F^{(x)}[p(X, \theta)]$.

(iii) Execute back projection by taking inverse Fourier transform of the filtered spectrum.

Further, the following formula (26) is obtained from the formula (25).

$$f(x, y) = \int_{-\infty}^{\infty}\int_{0}^{\pi} \mathcal{F}_{(X)}\left[\frac{\partial p(X, \theta)}{\partial X}\right]\left(-i\frac{|\rho|}{\rho}\right)\exp[i\rho X]d\rho d\theta \quad (26)$$

Given that a result obtained by differentiating p(X, θ) with respect to X is called a projection differential image, it is understood from the formula (26) that the tomographic image is obtained from the projection differential image through the following operations.

(i) Take Fourier transform of each projection differential image ∂p(X, θ)/∂x.

(ii) Multiply a frequency filter −i|ρ|/ρ by the obtained spectrum $F_{(x)}[\partial p(X, \theta)/\partial X]$.

(iii) Execute back projection by taking inverse Fourier transform of the filtered spectrum.

In addition to the image reconstruction methods expressed by the formulae (25) and (26), other methods using frequency filters in different forms are also called the FBP methods and are commonly known. Those FBP methods using frequency filters different from the frequency filters in the formulae (25) and (26) may be further optionally employed in this EXAMPLE.

The method of obtaining the tomographic image with the FBP method has been described above. The relationship between a projection differential phase image $\partial_p(X, \theta, z)/\partial X$, which is obtained from the moiré detectable by the Talbot interferometer, and a tomographic phase image Φ(x, y, z) of the specimen is expressed by the following formula (27) on the basis of the formula (20):

$$\frac{\partial p(X, \theta, z)}{\partial X} = \int_{-\infty}^{\infty} \frac{\partial \Phi(X, Y, z)}{\partial X}dY \quad (27)$$

Figure 17B:
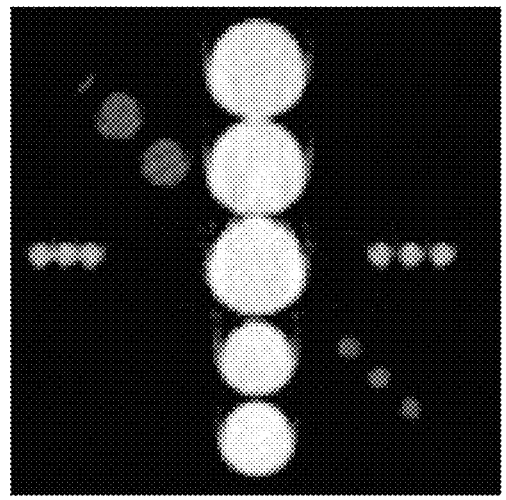
Figure 17C:
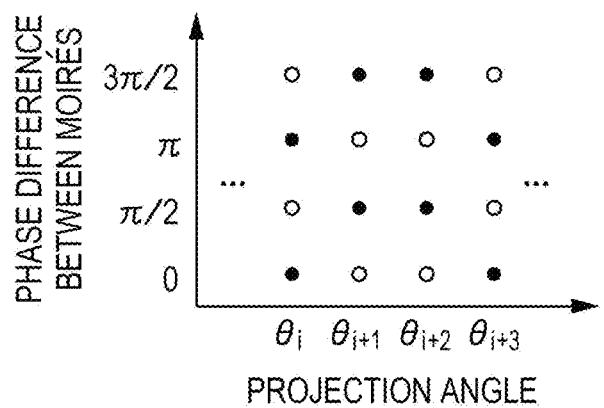

Thus, the tomographic phase image Φ(x, y, z) is obtained from the projection differential phase image by using the formula (26). Alternatively, the tomographic phase image Φ(x, y, z) may be obtained from the formula (25) after integrating individual projection differential phase images and obtaining the projection differential phase images. FIG. 17B illustrates the tomographic phase image of the specimen obtained in EXAMPLE 6.

As is apparent from the above description, the process of obtaining the projection image with the periodic pattern and the process of obtaining the tomographic image from the projection image are independently of each other. Accordingly, the image reconstruction method of obtaining the tomographic image from the projection image is not limited to the FBP method, and various image reconstruction methods may be optionally used in combination with the present disclosure.

Moreover, as described above, an absorption image and a scattering image of the specimen are further obtained with the Talbot interferometer (or the Talbot-Lau interferometer) in addition to the differential phase image. Here, the absorption image and the scattering image thus obtained are called respectively a projection absorption image and a projection scattering image, and tomographic images corresponding to absorption and scattering are called respectively a tomographic absorption image and a tomographic scattering image. The tomographic absorption image and the tomographic scattering image are obtained respectively from the projection absorption image and the projection scattering image by using the formula (25) in a similar manner to that used for obtaining the tomographic phase image from the projection differential phase image.

Comparative Example 5

Figure 24A:
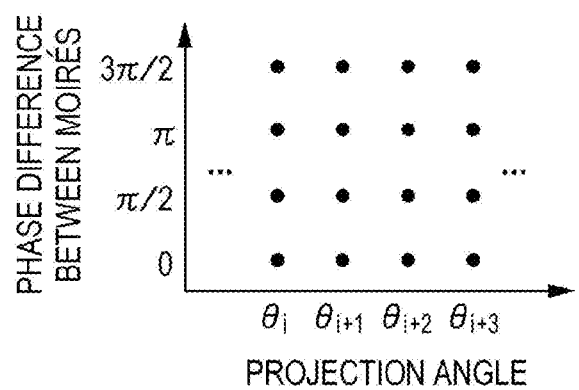
FIGS. 24A to 24D illustrate moiré acquisition manners and simulation results in COMPARATIVE EXAMPLES 5 and 6.
Figure 24B:
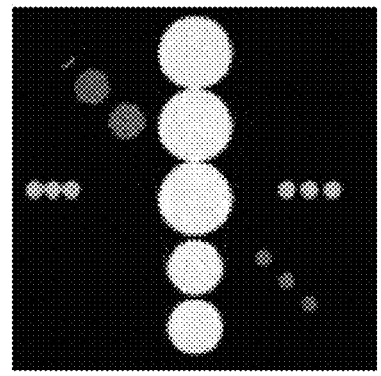

COMPARATIVE EXAMPLE 5 will be described below in connection with an example in which a tomographic phase image is obtained from projection differential phase images of a specimen, which are obtained with the phase shifting method. Also in COMPARATIVE EXAMPLE 5, the specimen is rotated through 180 degrees in units of 1.40625 degrees, and images of the specimen are taken from 128 directions. COMPARATIVE EXAMPLE 5 differs from EXAMPLE 6 in detecting four moirés in total, i.e., a reference moiré and moirés having phases shifted respectively by $\pi/2$, $\pi$ and $3\pi/2$ in the X-direction with respect to the reference moiré, at each projection angle. FIG. 24A illustrates the concept of setting the position where the moiré is detected at each projection angle. The projection differential phase image in the X-direction at each projection angle is obtained from the detected moirés in a similar manner to that used for obtaining the projection differential phase image in COMPARATIVE EXAMPLE 1. More specifically, projection differential phase images in 128 directions are obtained from 512 moirés. The tomographic phase image of the specimen is obtained from the projection differential phase images in 128 directions in accordance with the formula (26). FIG. 24B illustrates the tomographic phase image of the specimen obtained in COMPARATIVE EXAMPLE 5.

Comparative Example 6

Figure 24C:
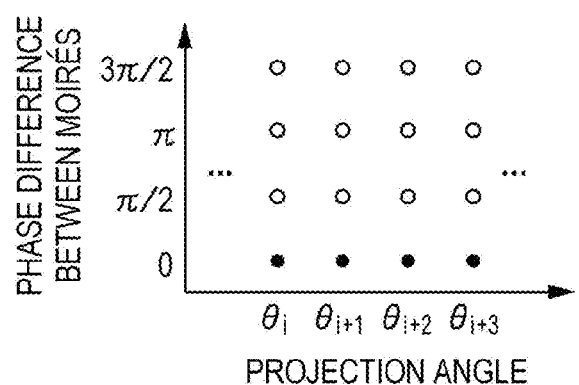
Figure 24D:
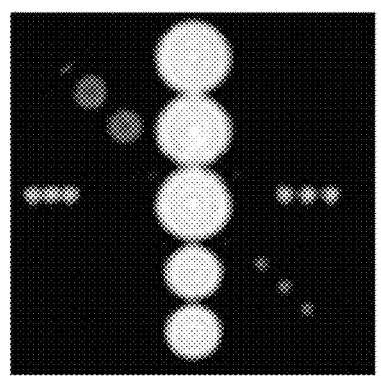

COMPARATIVE EXAMPLE 6 will be described below in connection with an example in which a tomographic phase image is obtained from projection differential phase images of a specimen, which are obtained with the windowed Fourier method. Also in COMPARATIVE EXAMPLE 6, the specimen is rotated through 180 degrees in units of 1.40625 degrees, and images of the specimen are taken from 128 directions. However, one moiré is detected at each projection angle. FIG. 24C illustrates the concept of setting the position where the moiré is detected. The projection differential phase image in the X-direction at each projection image is obtained from the detected moiré in a similar manner to that used for obtaining the projection differential phase image in COMPARATIVE EXAMPLE 2. More specifically, projection differential phase images in 128 directions are obtained from 128 moirés. The tomographic phase image of the specimen is obtained from the projection differential phase images in 128 directions in accordance with the formula (26). FIG. 24D illustrates the tomographic phase image of the specimen obtained in COMPARATIVE EXAMPLE 6.

Figure 18:
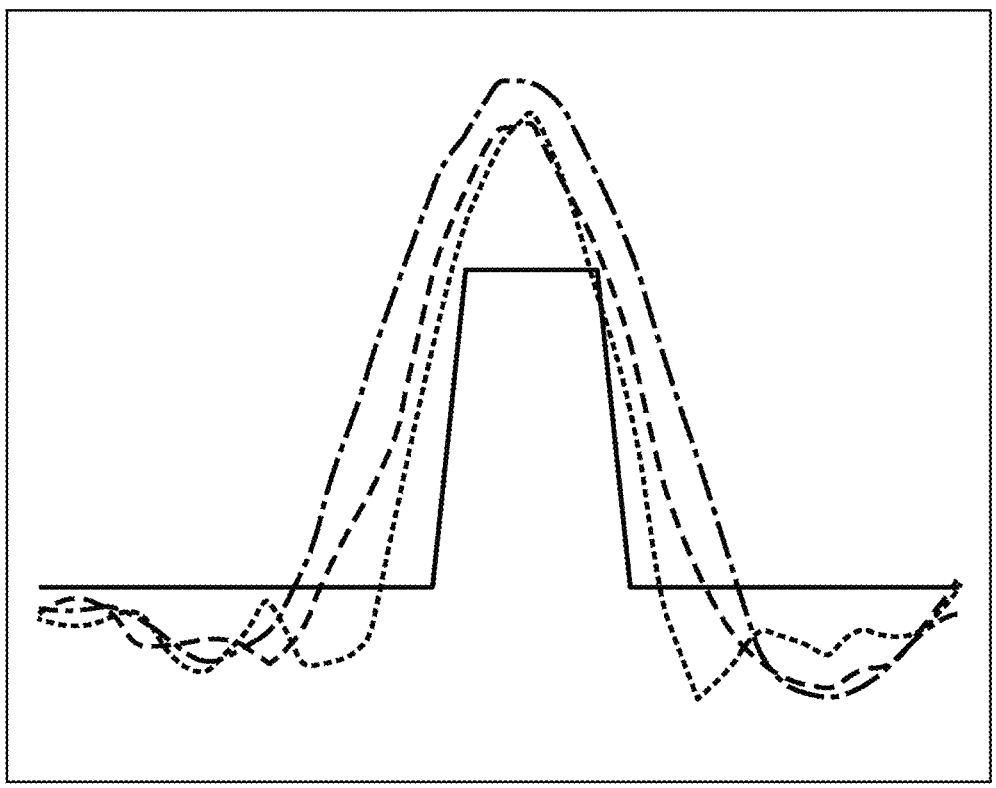
FIG. 18 illustrates line profiles as simulation results in EXAMPLE 6 and COMPARATIVE EXAMPLES 5 and 6.

FIG. 18 illustrate line profiles in respective portions, which are denoted by dots in FIGS. 17B, 24B and 24D, for comparison of spatial resolution among the tomographic phase images obtained in EXAMPLE 6, COMPARATIVE EXAMPLE 5, and COMPARATIVE EXAMPLE 6. In FIG. 18, a dotted line represents the line profile of the tomographic phase image obtained in EXAMPLE 6, and a broken line represents the line profile of the tomographic phase image obtained in COMPARATIVE EXAMPLE 5. A one-dot-chain line represents the line profile of the tomographic phase image obtained in COMPARATIVE EXAMPLE 5, and a solid line represents the line profile of a true tomographic phase image of the specimen. As seen from those line profiles, the tomographic phase image more closely approaching to the true tomographic phase image is obtained in successive order of COMPARATIVE EXAMPLE 6, EXAMPLE 6, and COMPARATIVE EXAMPLE 5. Thus, the spatial resolution is improved in that order.

EXAMPLE 7

Figure 19A:
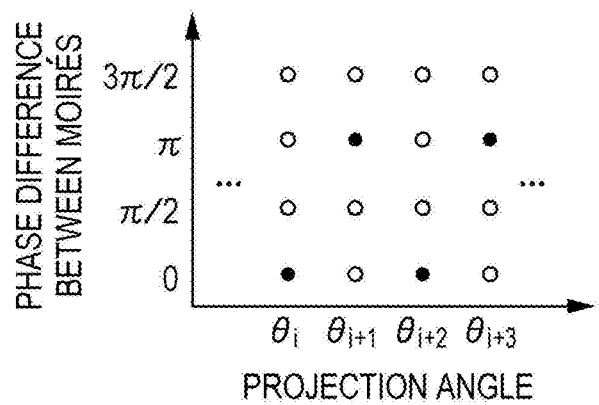
FIGS. 19A to 19C illustrate a moiré acquisition manner and a simulation result in EXAMPLE 7.

EXAMPLE 7 will be described below in connection with an example in which moirés are detected by a method different from that used in EXAMPLE 6, projection differential phase images are obtained from the those moirés by using the analytical method described in the first embodiment, and a tomographic phase image is obtained from the projection differential phase images. However, the method of obtaining the tomographic phase image from the projection differential phase images is similar to that in EXAMPLE 6. The method of detecting the moirés in EXAMPLE 7 has solved a problem with the above-described method of detecting the moirés in EXAMPLE 6. The method in EXAMPLE 6 has the problem that, because plural moirés are detected at each projection angle, the rotation of the specimen is to be stopped at each of the projection angles. In EXAMPLE 7, one moiré is detected at each projection angle so that the rotation of the specimen is not stopped during a series of operations of taking images of the specimen. Stated another way, the method of detecting the moirés, described in this EXAMPLE, enables images of the specimen to be taken to obtain the tomographic image while the specimen is continuously rotated. FIG. 19A illustrates the position where the moiré is detected at each projection angle in this EXAMPLE. Two types of methods of obtaining the projection differential phase image are described here.

The first method of obtaining the projection differential phase image is as follows. FIG. 19A is a conceptual illustration similar to FIG. 17A. The moiré is detected at each of positions of the projection angle and the phase difference, which are indicated by black circles (●) in FIG. 19A, while the moiré is not detected at each of positions of the projection angle and the phase difference, which are indicated by white circles (○) in FIG. 19A. As illustrated in FIG. 19A, a first moiré serving as a reference is first obtained at a first projection angle $\theta_i$. Next, a second moiré is obtained at a second projection angle $\theta_{i+1}$. A phase of the second moiré is shifted by $\pi$ in a direction, which is perpendicular to both the rotation axis of the specimen and the projection direction, with respect to the reference moiré. A projection differential phase image at the projection angle $\theta_i$ is obtained from those two moirés by using the analytical method used in the first embodiment. In more detail, a third moiré, which is a virtual moiré, is obtained from the first moiré, and a fourth moiré, which is a virtual moiré, is obtained from the second moiré. A projection differential phase image is obtained at the first projection angle $\theta_i$ from those four moirés in total. Similarly, a projection differential phase image at a third projection angle $\theta_{i+2}$ is obtained from moirés that are detected at the third projection angle $\theta_{i+2}$ and a fourth projection angle $\theta_{i+3}$. Projection differential phase images are not obtained at the second and fourth projection angles $\theta_{i+1}$ and $\theta_{i+3}$. Thus, the number of the obtained projection differential phase images is a half that of the detected moirés. Alternatively, a projection differential phase image at the second projection angle $\theta_{i+1}$ may be obtained from the moirés detected at the first and second projection angles $\theta_i$ and $\theta_{i+1}$, and a projection differential phase image at the fourth projection angle $\theta_{i+3}$ may be obtained from the moirés detected at the third and fourth projection angles $\theta_{i+2}$ and $\theta_{i+3}$. While FIG. 19A illustrates the case where the moirés detected at the first projection angle $\theta_i$ and the third projection angle $\theta_{i+2}$ have the phase difference of 0, the phase difference is not always to be 0. As another example, the moirés may be detected at the projection angles and the phase differences illustrated in FIG. 19C.

The second method of obtaining the projection differential phase image is as follows. In the second method, the projection differential phase images at the second projection angle $\theta_{i+1}$ and the fourth projection angle $\theta_{i+3}$ are also obtained. The projection angles and the phase differences at which the moirés are detected are the same as those illustrated in FIG. 19A. Further, a manner of obtaining the projection differential phase image at each of the first projection angle $\theta_i$ and the third projection angle $\theta_{i+2}$ is also the same as that in the first method. According to the second method, however, a projection differential phase image at the second projection angle $\theta_{i+1}$ is obtained from the moirés that are detected at the second projection angle $\theta_{i+1}$ and the third projection angle $\theta_{i+2}$. Similarly, a projection differential phase image at the fourth projection angle $\theta_{i+3}$ is obtained from the moirés that are detected at the fourth projection angle $\theta_{i+3}$ and a fifth projection angle $\theta_{i+4}$. A manner of obtaining the projection differential phase image at the fifth projection angle $\theta_{i+4}$ is the same as that of obtaining the projection differential phase image at each of the first projection angle $\theta i$ and the third projection angle $\theta_{i+2}$ in the first method. In the second method, because the projection differential phase image at the second projection angle $\theta_{i+1}$ is obtained, the moiré detected at the second projection angle $\theta_{i+1}$ is to be shifted in phase by $\pi$ with respect to the moiré detected at the third projection angle $\theta_{i+2}$. In the second method, the number of the obtained projection differential phase images is equal to that of the detected moirés.

The above-described two methods of obtaining the projection differential phase image are each a method of handling moirés detected at different projection angles as if those moirés are detected at the same projection angle. Comparing with the method described in EXAMPLE 6, therefore, distortion or blur of an image may occur, but EXAMPLE 7 is beneficial in that, as described above, the rotation of the apparatus is not stopped during a series of the image taking operations.

Figure 19B:
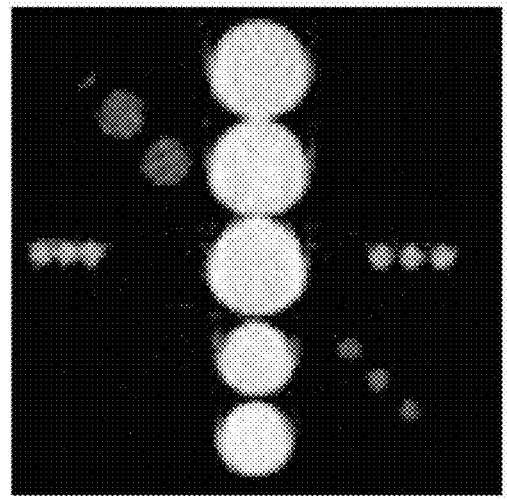
Figure 19C:
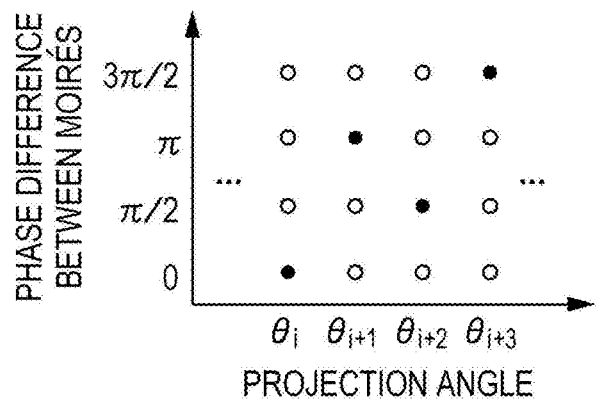

A simulation is executed to obtain a tomographic phase image from the projection differential phase images each of which has been obtained with the above-described first method. The wavefront measuring apparatus and the specimen both used in this simulation are the same as those used EXAMPLE 6. Further, as in EXAMPLE 6, the specimen is rotated through 180 degrees in units of 1.40625 degrees, and images of the specimen are taken from 128 directions. However, one moiré is detected at each projection angle, and the moiré detected at each projection angle has the phase difference as per described above in this EXAMPLE with reference to FIG. 19A. FIG. 19B illustrates the tomographic phase image obtained from the projection differential phase images in 64 directions, which have been obtained from the moirés taken in the 128 directions, in accordance with the formula (26).

Comparative Example 7

COMPARATIVE EXAMPLE 7 will be described below in connection with an example in which projection differential phase images are each obtained from moirés, which are obtained by a method different from that used in COMPARATIVE EXAMPLE 5, by employing the phase shifting method, and a tomographic image is obtained from the projection differential phase images. Two types of methods of obtaining the projection differential phase image are described here.

Figure 25A:
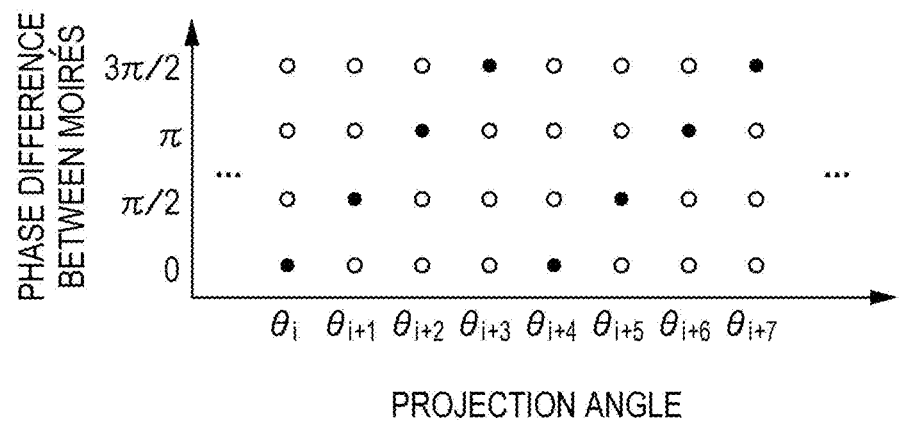
FIGS. 25A and 25B illustrate a moiré acquisition manner and a simulation result in COMPARATIVE EXAMPLE 7.

A first method of obtaining the projection differential phase image is as follows. This first method is described in I. Zanette, et al., Applied Physics Letters 98, 094101 (2011). FIG. 25A illustrates a position where a moiré is detected at each projection angle. As in FIG. 17A, FIG. 25A represents that the moiré is detected at each of positions of the projection angle and the phase difference, which are indicated by black circles (●) in FIG. 25A, while the moiré is not detected at each of positions of the projection angle and the phase difference, which are indicated by white circles (○) in FIG. 25A. In more detail, a first moiré serving as a reference is first obtained at a first projection angle $\theta_1$. Next, a second moiré is obtained at a second projection angle $\theta_{i+1}$. A phase of the second moiré is shifted by $\pi/2$ in a direction, which is perpendicular to the rotation axis of the specimen, with respect to the reference moiré. Next, a third moiré is obtained at a third projection angle $\theta_{i+2}$. A phase of the third moiré is shifted by $\pi$ in the direction, which is perpendicular to the rotation axis of the specimen, with respect to the reference moiré. Moreover, a fourth moiré is obtained at a fourth projection angle $\theta_{i+3}$. A phase of the fourth moiré is shifted by $3\pi/2$ in the direction, which is perpendicular to the rotation axis of the specimen, with respect to the reference moiré. A projection differential phase image at the projection angle $\theta_i$ is obtained from those four detected moirés by using the analytical method used in COMPARATIVE EXAMPLE 1. Similarly, a projection differential phase image at a fifth projection angle $\theta_{i+4}$ is obtained. While FIG. 25A illustrates the case where the phase difference between the moirés detected at the first projection angle $\theta_i$ and the fifth projection angle $\theta_{i+4}$ is 0, the phase difference therebetween is not always to be 0. In this first method, projection differential phase images are not obtained at the second, third and fourth projection angles $\theta_{i+1}$, $\theta_{i+2}$ and $\theta_{i+3}$. Thus, the number of the obtained projection differential phase images is ¼ of the number of the detected moirés.

The second method of obtaining the projection differential phase image is as follows. In the second method, the projection differential phase images at the second, third and fourth projection angles $\theta_{i+1}$, $\theta_{i+2}$ and $\theta_{i+3}$ are also obtained. The projection angles and the phase differences at which the moirés are detected are the same as those illustrated in FIG. 25A. Further, a manner of obtaining the projection differential phase image at the first projection angle $\theta_i$ is also the same as that in the first method. In the second method, however, the projection differential phase image at the second projection angle $\theta_{i+1}$ is obtained from the moirés that are detected at the projection angles $\theta_{i+1}$, $\theta_{i+2}$, $\theta_{i+3}$ and $\theta_{i+4}$. Similarly, projection differential phase images at the projection angles $\theta_{i+2}$ and $\theta_{i+3}$ are further obtained. For that reason, a phase of the moiré detected at the fifth projection angle $\theta_{i+4}$ is beneficially shifted by $\pi/2$ from that of the moiré detected at the fourth projection angle $\theta_{i+3}$. In the second method, the number of the obtained projection differential phase images is equal to that of the detected moirés.

Figure 25B:
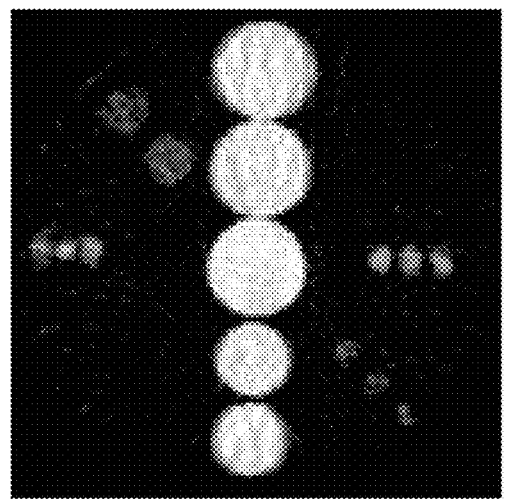

A simulation is executed to obtain a tomographic phase image from the projection differential phase images each of which has been obtained with the above-described first method. The wavefront measuring apparatus and the specimen both used in this simulation are the same as those used EXAMPLE 6. Further, as in EXAMPLE 6, the specimen is rotated through 180 degrees in units of 1.40625 degrees, and images of the specimen are taken from 128 directions. However, one moiré is detected at each projection angle, and the moiré detected at each projection angle has the phase difference as per described above in this COMPARATIVE EXAMPLE. FIG. 25B illustrates the tomographic phase image obtained from the projection differential phase images in 32 directions, which have been obtained from the moirés taken in the 128 directions, in accordance with the formula (26).

EXAMPLE 7 and COMPARATIVE EXAMPLE 7 differ from EXAMPLE 6, COMPARATIVE EXAMPLE 5 and COMPARATIVE EXAMPLE 6 in that the projection differential phase image is obtained by handling the moirés, which are obtained at different projection angles, as the moirés obtained at the same projection angle. Therefore, particularly when the interval between the projection angles is relatively wide, there is a possibility that distortion or blur of the image may occur at a point away from the rotation center of the specimen. Comparing EXAMPLE 7 and COMPARATIVE EXAMPLE 7, EXAMPLE 7 is more effective in reducing such a possibility. In COMPARATIVE EXAMPLE 7, the projection differential phase image at one projection angle is obtained from the moirés detected at four projection angles. On the other hand, in EXAMPLE 7, the projection differential phase image at one projection angle is obtained from the moirés detected at two projection angles. Accordingly, even when distortion or blur of the image occurs, an influence of the distortion or the blur is reduced. As described above, the wavefront measuring method according to the first embodiment is also applied to the case of obtaining a tomographic image. While, in EXAMPLES 6 and 7, the projection differential phase image is obtained with the method, which has been described in the first embodiment, based on the phase shifting method, the projection differential phase image may be obtained with the method, which has been described in the second embodiment, based on the windowed Fourier method, and the tomographic phase image may be obtained from that projection differential phase image.

Aspects of the present disclosure can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., non-transitory computer-readable medium).

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. A wavefront information obtaining method comprising:
receiving intensity information of a first periodic pattern and intensity information of a second periodic pattern having a phase shifted with respect to a phase of the first periodic pattern; and
obtaining wavefront information,
wherein the obtaining of the wavefront information obtains the wavefront information for one pixel by using:
intensity information at a first pixel of the first periodic pattern;
intensity information at a second pixel of the first periodic pattern, the second pixel being positioned within three pixels from the first pixel; and
intensity information at the first pixel of the second periodic pattern.

2. The wavefront information obtaining method according to claim 1, wherein the obtaining of the wavefront information obtains the wavefront information by applying:
the intensity information at the first pixel of the first periodic pattern;
the intensity information at the second pixel of the first periodic pattern; and
the intensity information at the first pixel of the second periodic pattern,
to a formula based on a phase shifting method on condition that those pieces of intensity information are regarded as pieces of intensity information at the first pixel of different periodic patterns.

3. The wavefront information obtaining method according to claim 1, wherein the obtaining of the wavefront information obtains the wavefront information by applying:
the intensity information at the first pixel of the first periodic pattern;
the intensity information at the second pixel of the first periodic pattern; and
the intensity information at the first pixel of the second periodic pattern,
to a formula based on a phase shifting method on condition that those pieces of intensity information are regarded as pieces of intensity information at the first pixel or the second pixel of different periodic patterns.

4. The wavefront information obtaining method according to claim 3, wherein the obtaining of the wavefront information obtains wavefront information for one pixel by using:
the intensity information at the first pixel of the first periodic pattern;
the intensity information at the second pixel of the first periodic pattern;
the intensity information at the first pixel of the second periodic pattern; and
intensity information at the second pixel of the second periodic pattern.

5. The wavefront information obtaining method according to claim 3, wherein the first pixel and the second pixel are adjacent to each other in the first and second periodic pattern.

6. The wavefront information obtaining method according to claim 1, wherein the obtaining of the wavefront information obtains the wavefront information by taking Fourier transform of a composite periodic pattern of an intensity distribution having:
an intensity at the first pixel of the first periodic pattern;
an intensity at the second pixel of the first periodic pattern; and
an intensity at the first pixel of the second periodic pattern.

7. The wavefront information obtaining method according to claim 6, wherein, in the composite periodic pattern,
the intensity at the first pixel of the first periodic pattern and the intensity at the first pixel of the second periodic pattern are positioned within three pixels.

8. The wavefront information obtaining method according to claim 1, wherein the wavefront information is information regarding at least one of a phase, a differential phase, an amplitude, and scattering of a wavefront of light which forms the first and second periodic pattern.

9. The wavefront information obtaining method according to claim 1, wherein the obtaining of the wavefront information obtains wavefront information for a plurality of pixels.

10. The wavefront information obtaining method according to claim 9, further comprising
transmitting, to a display apparatus, image data of the wavefront information for a plurality of pixels.

11. The wavefront information obtaining method according to claim 1, wherein the periodic pattern is an interference pattern or a moiré.

12. The wavefront information obtaining method according to claim 1, wherein the periodic pattern is an X-ray periodic pattern.

13. A non-transitory computer-readable medium storing a program for causing a computer to execute the wavefront information obtaining method according to claim 1.

14. A wavefront information obtaining method comprising:
receiving intensity information of a first periodic pattern, a second periodic pattern having a phase shifted in a first direction with respect to a phase of the first periodic pattern, and a third periodic pattern having a phase shifted in a second direction with respect to the phase of the first periodic pattern, the second direction crossing the first direction;
obtaining shearing wavefront information in the first direction; and
obtaining shearing wavefront information in the second direction,
wherein the obtaining the shearing wavefront information in the first direction obtains the shearing wavefront information in the first direction for one pixel by using:
intensity information at a first pixel of the first periodic pattern;
intensity information at the first pixel of the second periodic pattern; and
intensity information at a second pixel of the first periodic pattern or the second periodic pattern, the second pixel being positioned within three pixels from the first pixel, and
wherein the obtaining the shearing wavefront information in the second direction obtains the shearing wavefront information in the second direction for one pixel by using:
the intensity information at the first pixel of the first periodic pattern;
intensity information at the first pixel of the third periodic pattern; and
intensity information at a third pixel of the first periodic pattern or the third periodic pattern, the third pixel being positioned within three pixels from the first pixel.

15. A non-transitory computer-readable medium storing a program for causing a computer to execute the wavefront information obtaining method according to claim 14.

16. A computation apparatus configured to obtain wavefront information comprising:
a unit configured to receive intensity information of a first periodic pattern and intensity information of a second periodic pattern having a phase shifted with respect to a phase of the first periodic pattern; and
a unit configured to obtain wavefront information for one pixel in wavefront information distribution by using:
intensity at a first pixel of the first periodic pattern;
intensity at a second pixel of the first periodic pattern, the second pixel being positioned within three pixels from the first pixel; and
intensity at the first pixel of the second periodic pattern.

* * * * *